(12) United States Patent
Arimitsu et al.

(10) Patent No.: US 10,285,670 B2
(45) Date of Patent: May 14, 2019

(54) NEEDLE POSITIONING APPARATUS

(71) Applicants: Canon U.S.A., Inc., Melville, NY (US); The Brigham and Women's Hospital, Inc., Boston, MA (US)

(72) Inventors: Yasumichi Arimitsu, Yokohama (JP); Kazufumi Onuma, Kawasaki (JP); Takahisa Kato, Brookline, MA (US); Nobuhiko Hata, Newton, MA (US); Sang-Eun Song, Chestnut Hill, MA (US); Kemal Tuncali, Newton, MA (US); Junichi Tokuda, Newton, MA (US); Brian Ninni, Somerville, MA (US); Lydia Gayle Olson, Swamspcott, MA (US)

(73) Assignees: CANON U.S.A., INC., Melville, NY (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 617 days.

(21) Appl. No.: 14/851,987

(22) Filed: Sep. 11, 2015

(65) Prior Publication Data
US 2016/0074063 A1 Mar. 17, 2016

Related U.S. Application Data

(60) Provisional application No. 62/049,920, filed on Sep. 12, 2014.

(51) Int. Cl.
*A61B 10/02* (2006.01)
*A61B 5/055* (2006.01)
(Continued)

(52) U.S. Cl.
CPC .......... *A61B 10/0233* (2013.01); *A61B 5/055* (2013.01); *A61B 90/11* (2016.02);
(Continued)

(58) Field of Classification Search
CPC . A61B 90/11; A61B 17/3403; A61B 17/3405; A61B 17/3407; A61B 17/3409
See application file for complete search history.

(56) References Cited

U.S. PATENT DOCUMENTS

| 3,384,086 A | 5/1968 | Rocha-Miranda et al. |
| 4,841,967 A | 6/1989 | Chang et al. |

(Continued)

FOREIGN PATENT DOCUMENTS

| CA | 2784988 A1 | 2/2013 |
| DE | 2115121 A1 | 10/1972 |

(Continued)

OTHER PUBLICATIONS

U.S. Office Action issue in U.S. Appl. No. 14/799,021 dated Dec. 22, 2016.
(Continued)

*Primary Examiner* — Ashley L Fishback
(74) *Attorney, Agent, or Firm* — Canon USA Inc., IP Division

(57) ABSTRACT

A positioning apparatus including a needle holder having a through hole for regulating needle placement and movement, a needle positioning unit, and an engagement member that fixes a position of the needle holder with respect to the needle positioning unit. The needle holder is either least partially detachably attached to the needle positioning unit or deformable. The positioning apparatus may be designed to accommodate the placement of multiple needles.

21 Claims, 25 Drawing Sheets

(51) Int. Cl.
*A61B 90/11* (2016.01)
*A61B 17/00* (2006.01)
*A61B 17/34* (2006.01)
*A61B 90/00* (2016.01)

(52) U.S. Cl.
CPC .............. *A61B 2017/00911* (2013.01); *A61B 2017/3409* (2013.01); *A61B 2090/374* (2016.02); *A61B 2090/3954* (2016.02)

(56) References Cited

U.S. PATENT DOCUMENTS

| | | | |
|---|---|---|---|
| 4,883,053 A * | 11/1989 | Simon | A61B 17/3403 128/DIG. 26 |
| 5,196,019 A | 3/1993 | Davis et al. | |
| 5,201,742 A | 4/1993 | Hasson | |
| 5,280,427 A | 1/1994 | Magnusson et al. | |
| 5,427,099 A | 6/1995 | Adams | |
| 5,682,892 A | 11/1997 | Selder et al. | |
| 5,706,812 A | 1/1998 | Strenk et al. | |
| 5,957,934 A | 9/1999 | Rapoport | |
| 5,993,463 A | 11/1999 | Truwit | |
| 6,079,681 A | 6/2000 | Stern et al. | |
| 6,119,032 A | 9/2000 | Martin et al. | |
| 6,185,445 B1 | 2/2001 | Knuttel | |
| 6,529,764 B1 | 5/2003 | Kato et al. | |
| 6,676,669 B2 | 1/2004 | Charles et al. | |
| 6,975,896 B2 | 12/2005 | Ehnholm et al. | |
| 7,083,608 B2 | 8/2006 | Tomita et al. | |
| 7,187,104 B2 | 3/2007 | Yamamoto et al. | |
| 7,379,769 B2 | 5/2008 | Piron et al. | |
| 7,442,187 B2 | 10/2008 | Khayal et al. | |
| 7,636,596 B2 | 12/2009 | Solar | |
| 7,824,417 B2 | 11/2010 | Magnusson et al. | |
| 8,116,850 B2 | 2/2012 | Solar | |
| 8,241,301 B2 | 8/2012 | Zhang et al. | |
| 8,298,245 B2 | 10/2012 | Li et al. | |
| 8,308,740 B2 | 11/2012 | Tolley et al. | |
| 8,535,335 B2 | 9/2013 | Yi et al. | |
| 8,774,901 B2 | 7/2014 | Velusamy et al. | |
| 2001/0000940 A1 | 5/2001 | Maruyama | |
| 2002/0019641 A1 | 2/2002 | Truwit | |
| 2003/0078502 A1 | 4/2003 | Miyaki | |
| 2003/0107299 A1 | 6/2003 | Fujimoto | |
| 2004/0064148 A1 | 4/2004 | Daum et al. | |
| 2005/0216026 A1 | 9/2005 | Culbert | |
| 2005/0261581 A1 | 11/2005 | Hughes et al. | |
| 2006/0149147 A1 | 7/2006 | Yanof | |
| 2006/0229641 A1 | 10/2006 | Gupta et al. | |
| 2007/0191867 A1 | 8/2007 | Mazzocchi | |
| 2007/0276407 A1 | 11/2007 | Vogele | |
| 2008/0004481 A1 | 1/2008 | Bax | |
| 2008/0009743 A1 | 1/2008 | Hayaska | |
| 2008/0033356 A1 | 2/2008 | Kluge et al. | |
| 2008/0161829 A1 | 7/2008 | Kang | |
| 2008/0167663 A1 | 7/2008 | De Mathelin et al. | |
| 2008/0262433 A1 | 10/2008 | Chung et al. | |
| 2008/0275466 A1 | 11/2008 | Skakoon | |
| 2009/0018390 A1 | 1/2009 | Honda et al. | |
| 2009/0079431 A1 | 5/2009 | Piferi et al. | |
| 2009/0234369 A1 | 9/2009 | Bax et al. | |
| 2010/0010505 A1 | 1/2010 | Herlihy et al. | |
| 2010/0082040 A1 | 4/2010 | Sahni | |
| 2010/0168766 A1 | 7/2010 | Zeng et al. | |
| 2011/0190787 A1 | 8/2011 | Sahni | |
| 2011/0237881 A1 | 9/2011 | Kunz | |
| 2011/0251624 A1 | 10/2011 | Yi et al. | |
| 2012/0022368 A1 | 1/2012 | Brabrand et al. | |
| 2012/0143048 A1 | 6/2012 | Finlay | |
| 2013/0069651 A1 | 3/2013 | Luminani | |
| 2013/0345718 A1 | 12/2013 | Crawford | |
| 2014/0018822 A1* | 1/2014 | Main | A61B 17/3403 606/130 |
| 2014/0052154 A1 | 2/2014 | Griffiths et al. | |
| 2014/0121675 A1 | 5/2014 | Bax | |
| 2014/0128881 A1 | 5/2014 | Tyc | |
| 2014/0128883 A1 | 5/2014 | Piron et al. | |
| 2014/0200445 A1 | 7/2014 | Boezaart et al. | |
| 2014/0275978 A1 | 9/2014 | Fujimoto et al. | |
| 2014/0275979 A1 | 9/2014 | Fujimoto et al. | |
| 2014/0336670 A1 | 11/2014 | Braband et al. | |
| 2014/0350572 A1 | 11/2014 | Elhawary et al. | |
| 2015/0238266 A1 | 8/2015 | Fujimoto et al. | |
| 2017/0014200 A1 | 1/2017 | Onuma et al. | |
| 2017/0030557 A1 | 2/2017 | Chen et al. | |
| 2017/0071626 A1 | 3/2017 | Onuma et al. | |
| 2017/0258489 A1 | 9/2017 | Galili et al. | |

FOREIGN PATENT DOCUMENTS

| | | |
|---|---|---|
| DE | 19647516 A1 | 5/1998 |
| EP | 2193750 A1 | 6/2010 |
| EP | 2561821 A1 | 2/2013 |
| JP | H10-502566 A | 3/1998 |
| JP | H11-155880 A | 6/1999 |
| JP | 2001-104279 A | 4/2001 |
| JP | 2004320846 A | 11/2004 |
| JP | 2005083961 A | 3/2005 |
| JP | 2008237971 A | 10/2008 |
| WO | 2009157007 A1 | 12/2009 |
| WO | 2012178109 A1 | 12/2012 |
| WO | 2013084107 A2 | 6/2013 |
| WO | 2014152685 A1 | 9/2014 |
| WO | 2017/132505 A1 | 8/2017 |

OTHER PUBLICATIONS

U.S. Office Action issue in U.S. Appl. No. 13/836,708 dated Jan. 11, 2017.
U.S. Office Action issue in U.S. Appl. No. 13/836,708 dated Jun. 27, 2017.
U.S. Office Action issue in U.S. Appl. No. 14/632,991 date Mar. 23, 2017.
Fischer, G.S., et al., "MRI Guided Needle Insertion—Comparison of Four Technique", In Annual Scientific Conference of the Society of Interventional Radiology 31, 2006. (Abstract only).
Koethe, Y. et al., "Accuracy and efficacy of percutaneous biopsy and ablation using robotic assistance under computed tomography guidance: a phantom study", European Society of Radiology, 2013.
Maxio Brochure: Planning and Targeting for CT guided Procedures by Perfint.
Palmer, K., et al., "Development and evaluation of optical needle depth sensor for percutaneous diagnosis and therapies", Medical Imaging 2014: Image-Guided Procedures, Robotic Interventions, and Modeling, 2014, Proc. of SPIE vol. 9036, 90362M.
Perfin, Inc Maxio Robot—Features http://www.perfinthealthcare.com/MaxicoFeatures.asp Accessed Sep. 11, 2015.
Song, S., et al., "Biopsy Needle Artifact Localization in MRI-guided Robotic Transrectal Prostate Intervention," IEEE Transactions on Biomedical Engineering, Jul. 2012, vol. 57, No. 7.
Song, S.E., et al., "Design Evaluation of a Double Ring RCM Mechanism for Robotic Needle Guidance in MRI-guided Liver Interventions", International Conference on Intelligent Robots and Systems, Nov. 3-7, 2013, pp. 4078-4083, Tokyo, Japan.
Hata, N. et al.,"MRI-Compatible Manipulator With Remote-Center-of-Motion Control", J. Magn. Reson Imaging, May 2008, vol. 27, vol. 5.
U.S. Office Action issued in U.S. Appl. No. 14/804,824 dated May 14, 2018.

* cited by examiner

Fig. 6
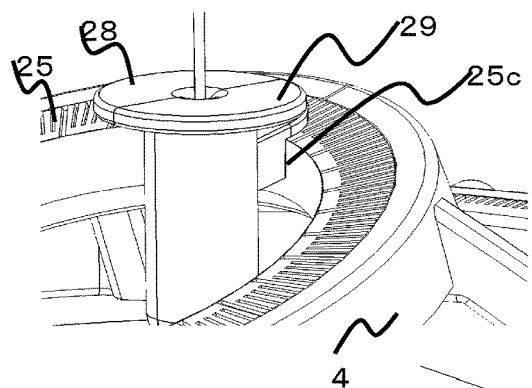
Fig. 8
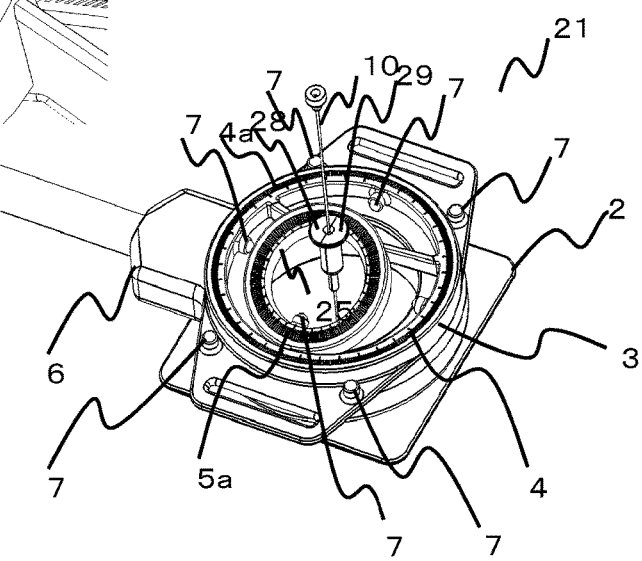
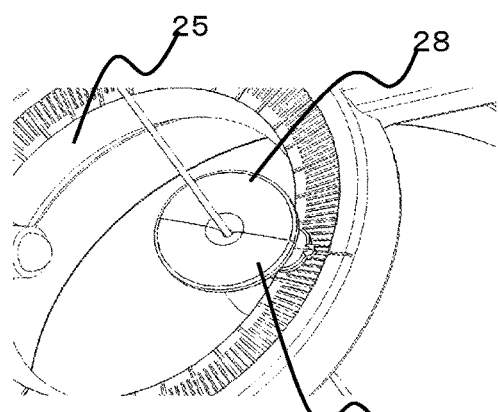
Fig. 7(a)
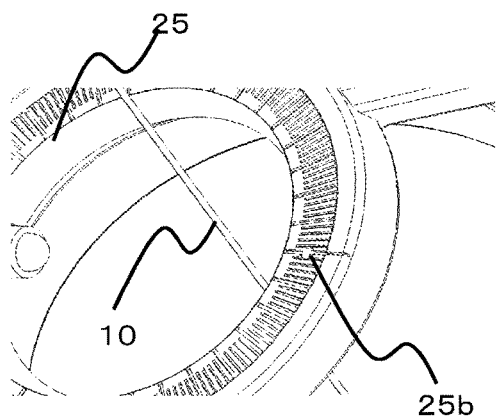
Fig. 7(b)

Fig. 9
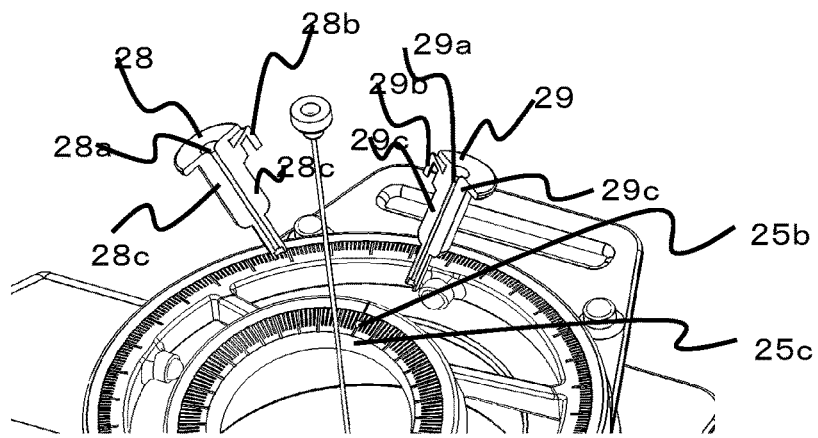
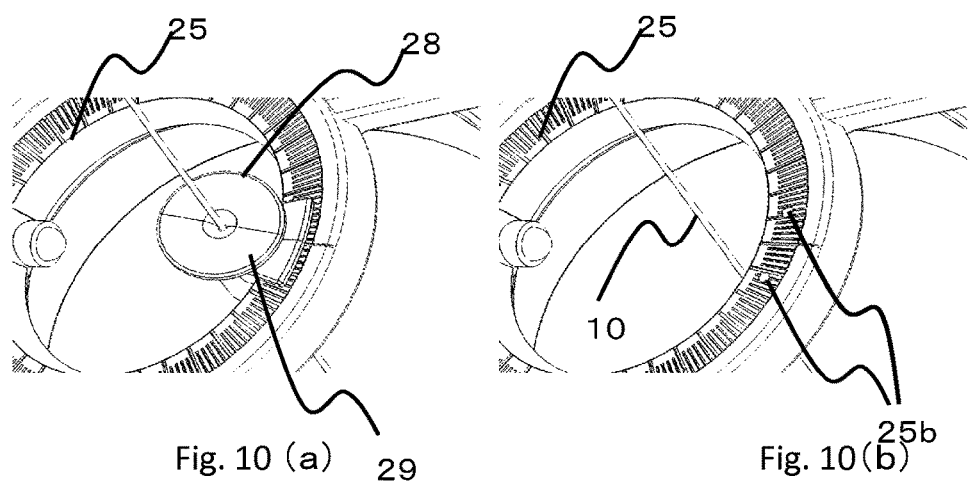
Fig. 10(a)  Fig. 10(b)
Fig. 11
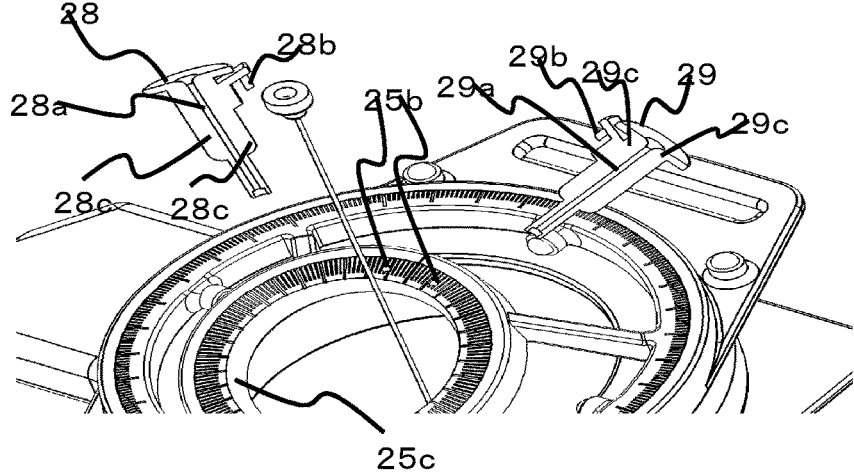

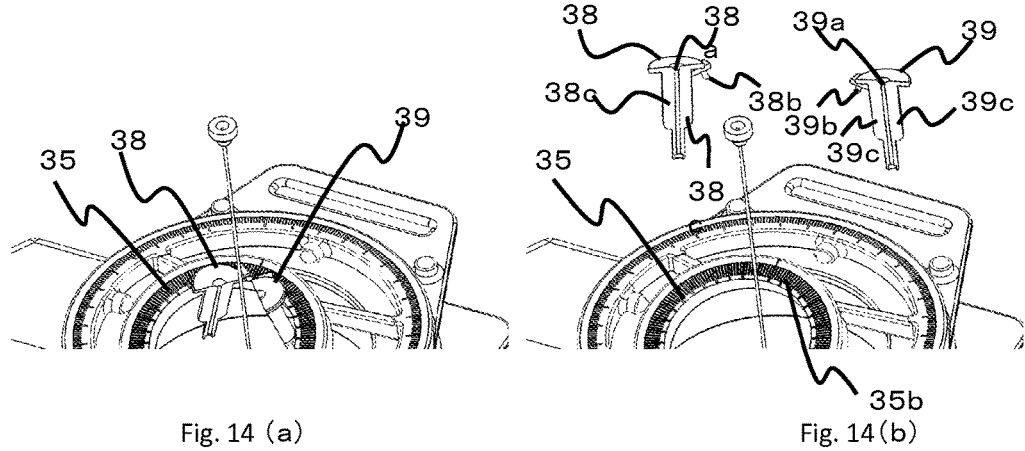
Fig. 14 (a)  Fig. 14(b)
Fig. 15
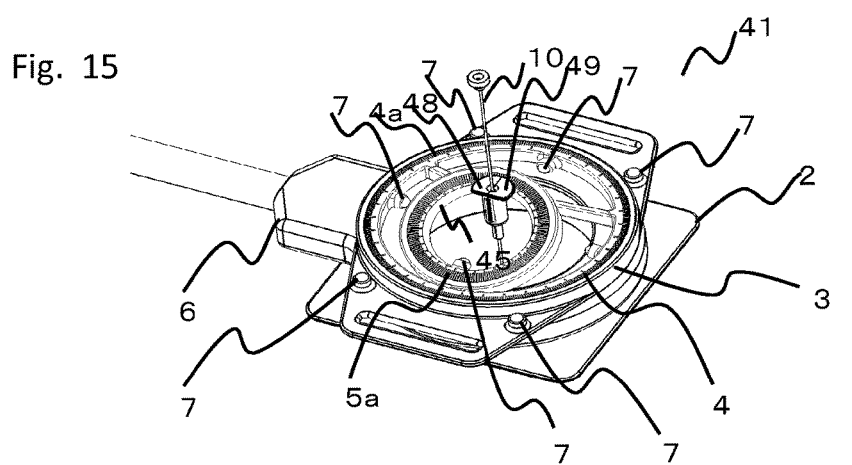
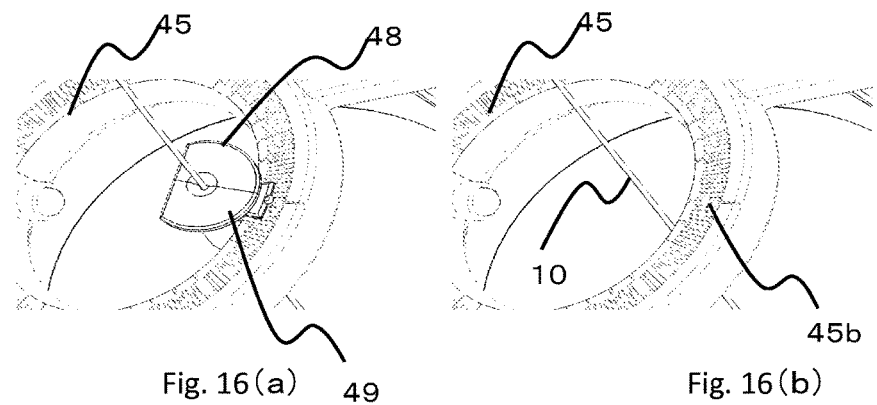
Fig. 16(a)  Fig. 16(b)

Fig. 17
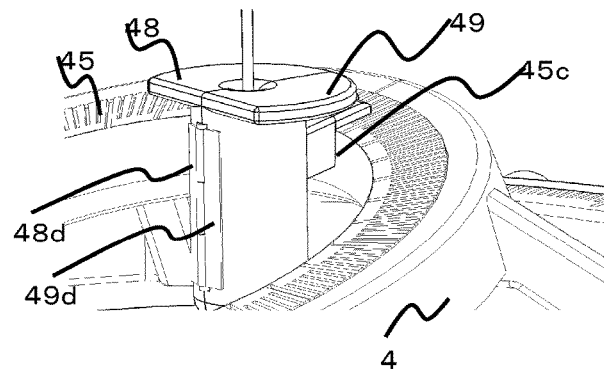
Fig. 18(a)  Fig. 18(b)
Fig. 19
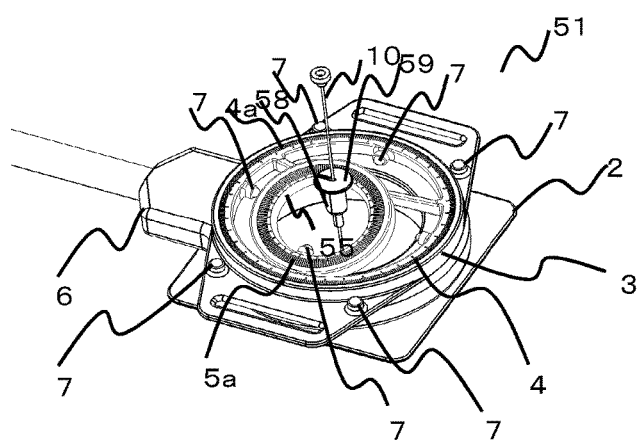

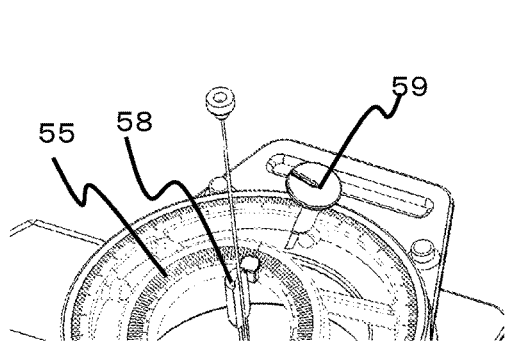
Fig. 23(a)
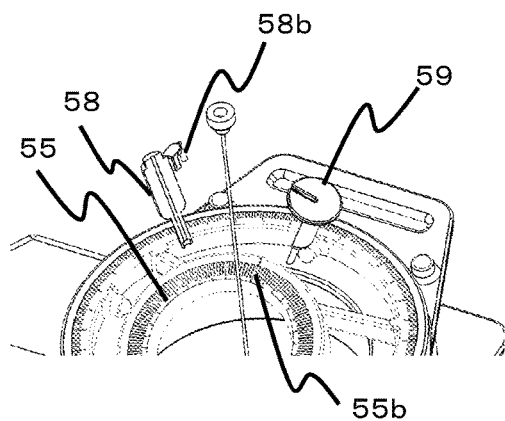
Fig. 23(b)
Fig. 24
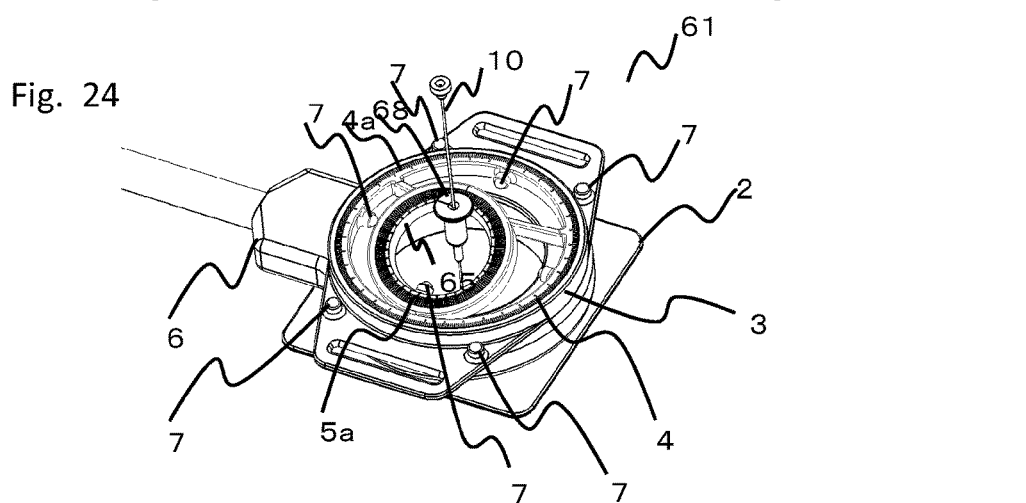
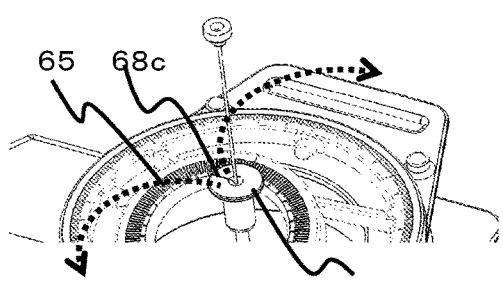
Fig. 25(a)
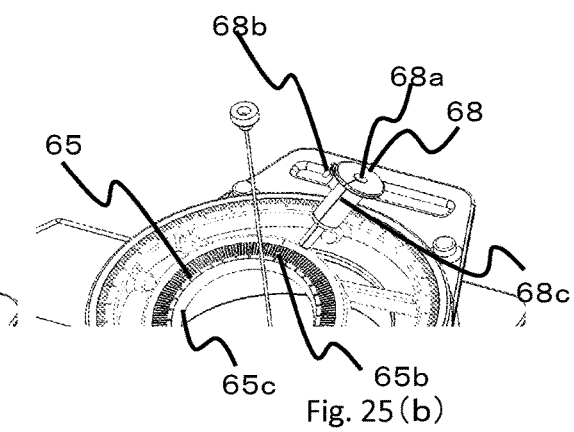
Fig. 25(b)

Fig. 26
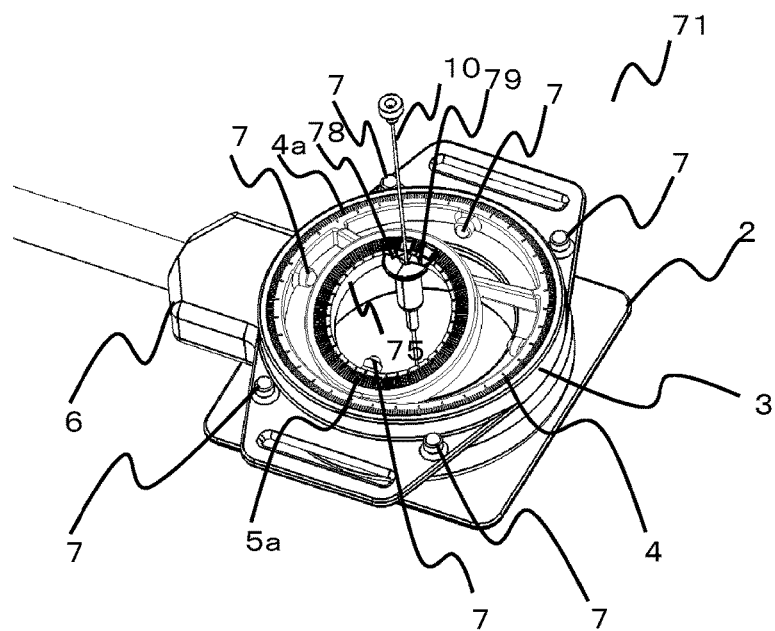
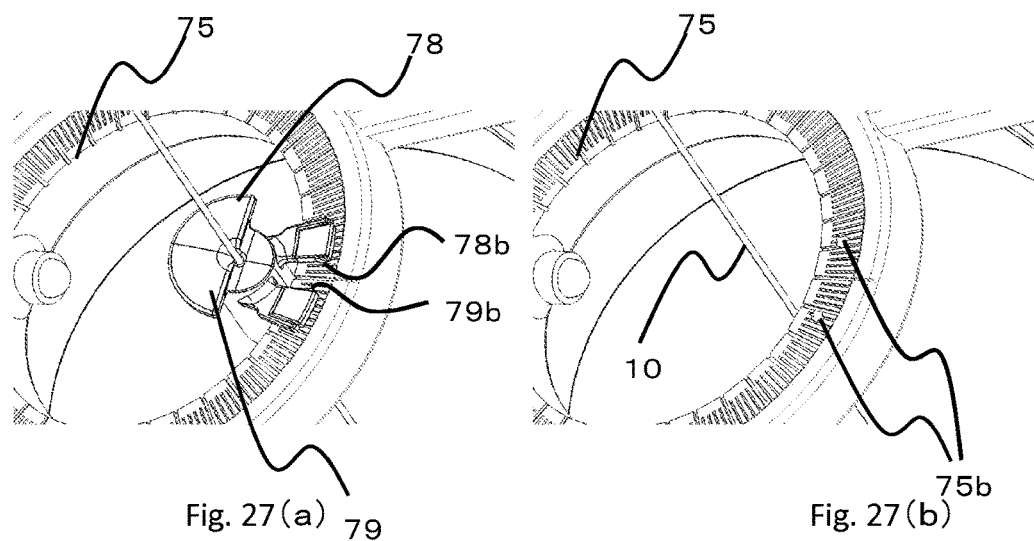
Fig. 27(a)  Fig. 27(b)

Fig. 28
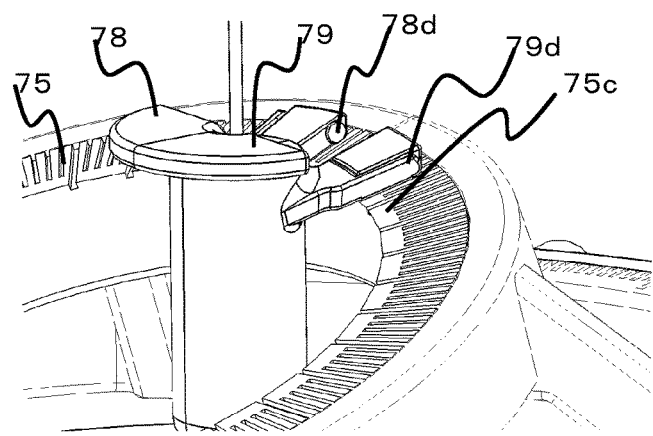
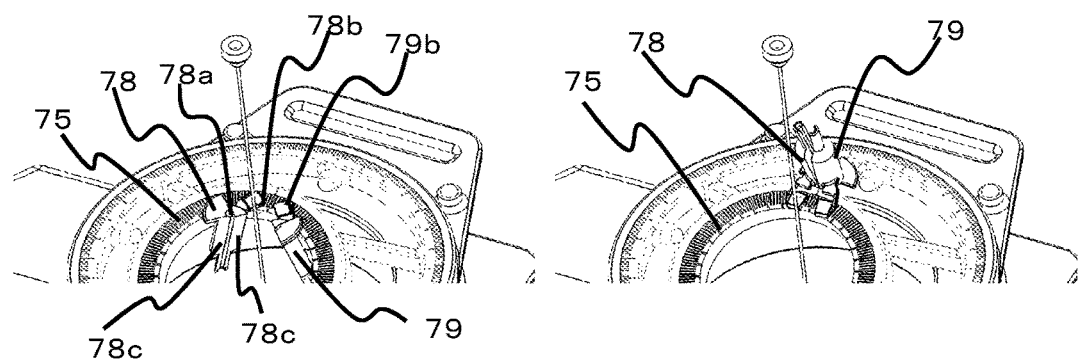
Fig. 29(a)　　　　　　　　　　　　　　　Fig. 29(b)
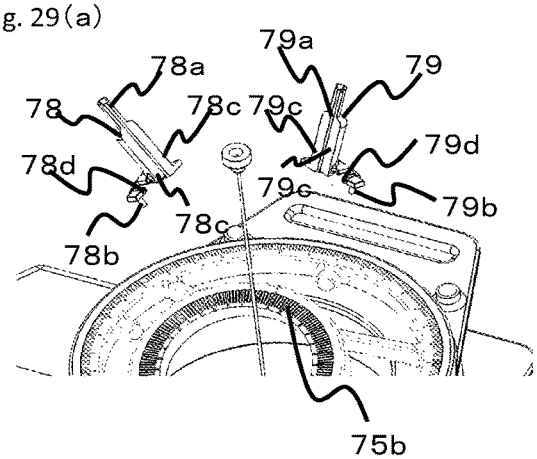
Fig. 29(c)

Fig. 30
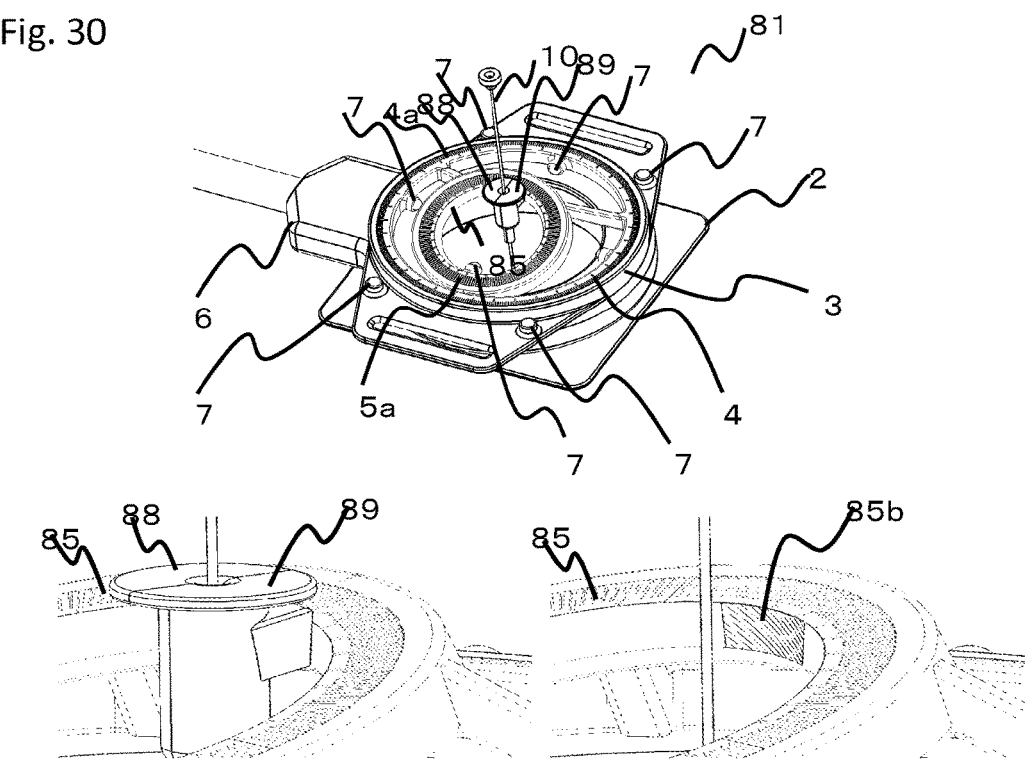
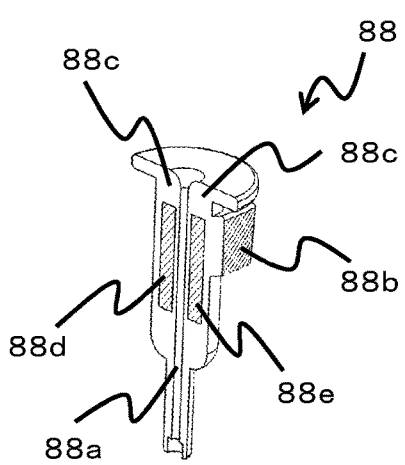
Fig. 31(a)
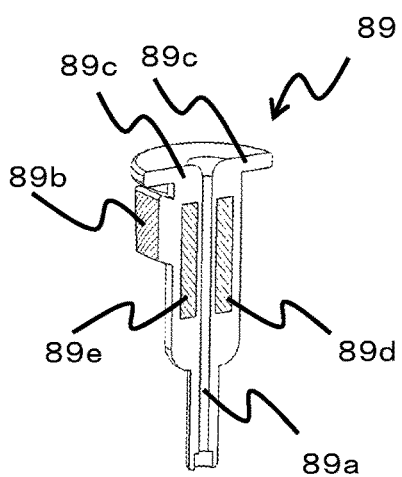
Fig. 31(b)
Fig. 32(a)
Fig. 32(b)

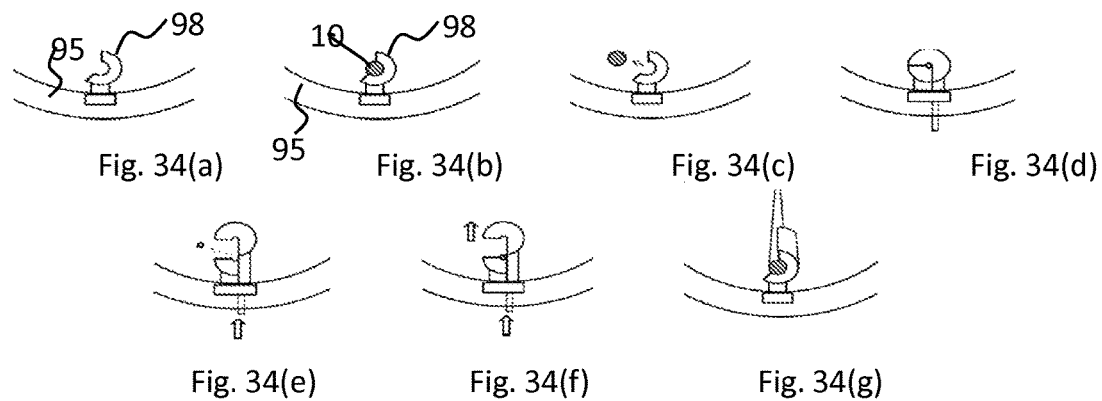
Fig. 34(a) Fig. 34(b) Fig. 34(c) Fig. 34(d)
Fig. 34(e) Fig. 34(f) Fig. 34(g)
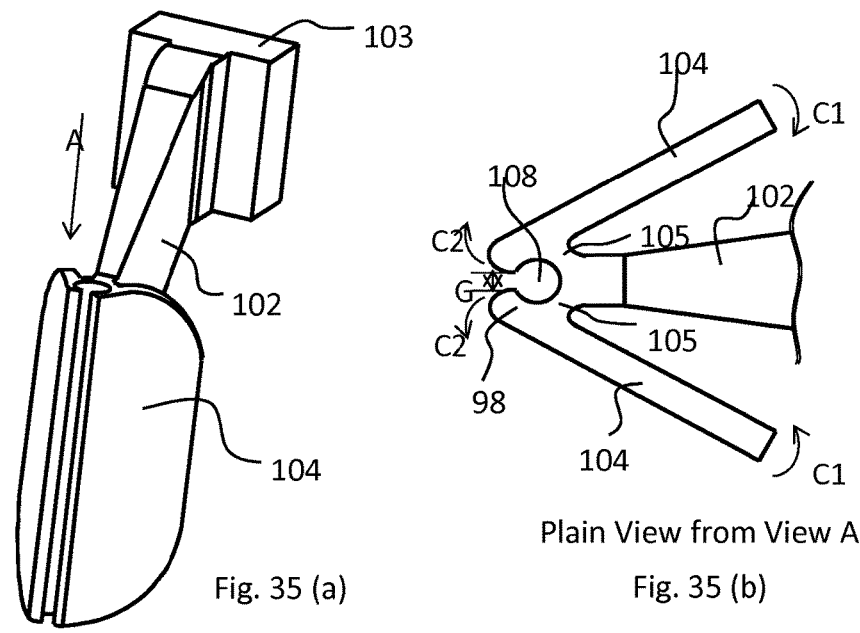
Fig. 35 (a)
Plain View from View A
Fig. 35 (b)

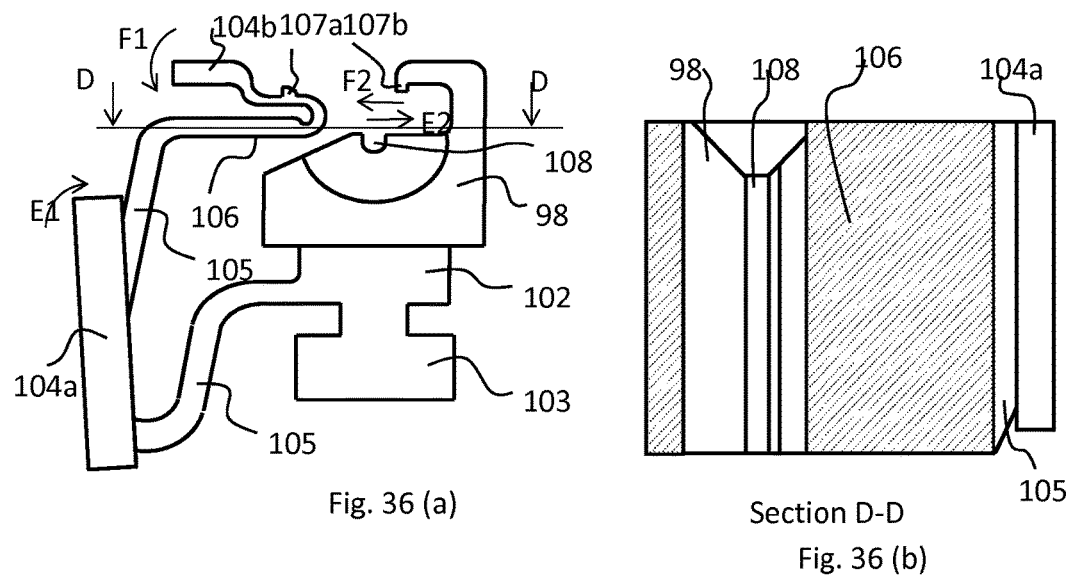
Fig. 36 (a)
Section D-D
Fig. 36 (b)
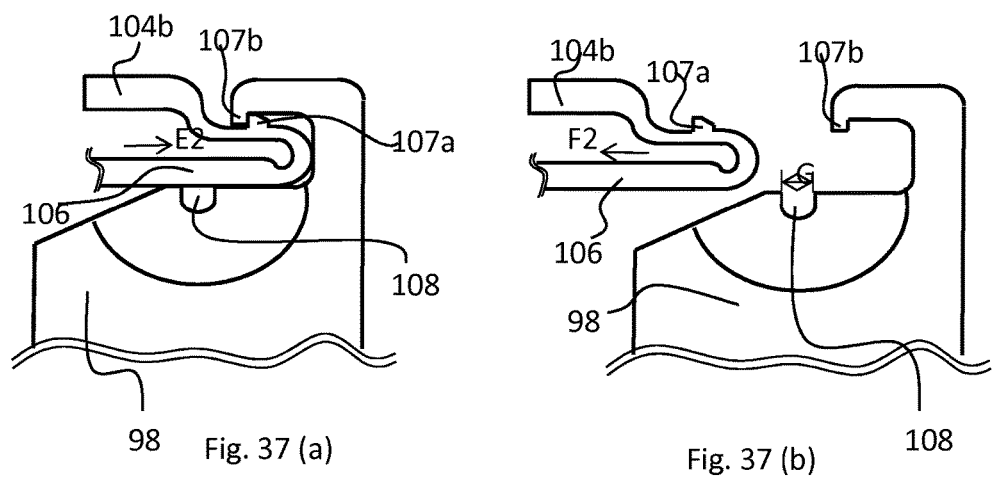
Fig. 37 (a)
Fig. 37 (b)

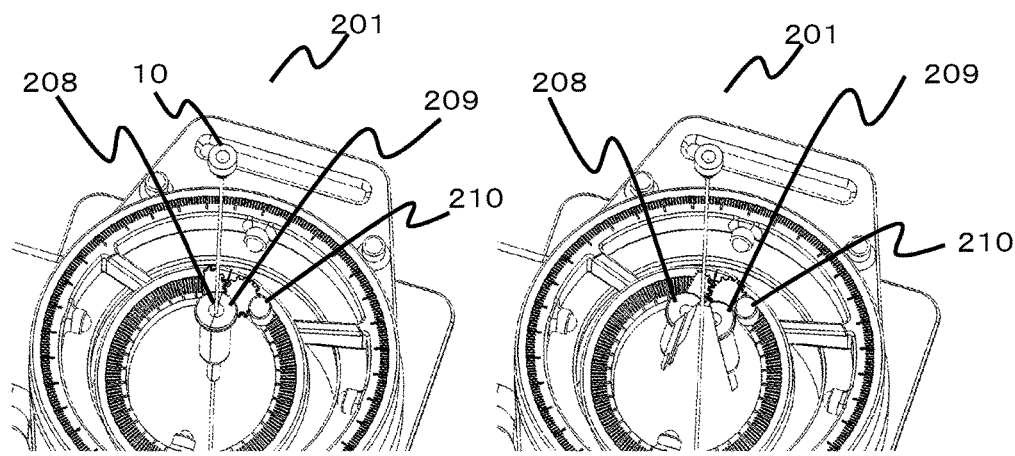
Fig. 44(a)  Fig. 44(b)
Fig. 44(c)
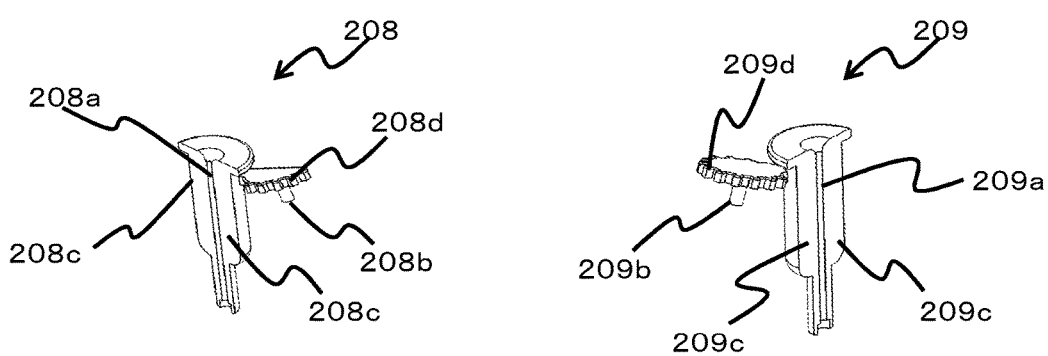
Fig. 45(a)  Fig. 45(b)

NEEDLE POSITIONING APPARATUS

CROSS-REFERENCE TO RELATED APPLICATIONS

This application claims priority to U.S. Provisional Application Ser. No. 62/049,920 filed Sep. 12, 2014 the content of which is incorporated herein by reference in its entirety.

FIELD OF THE DISCLOSURE

The disclosure of this application relates generally to medical devices, and in particular it relates to a needle positioning apparatuses for holding and positioning one or more needles, and more particularly, to a needle positioning apparatus suitable for minimally invasive puncture treatment.

BACKGROUND OF THE INVENTION

Percutaneous puncture treatment, in which a needle is guided to the affected part, is a typical example of minimally invasive treatment that is commonly performed. Examples of puncture treatments include ablation treatment in which a tumor or cancer cells are burned with radio waves and cryotherapy in which a tumor or cancer cells are frozen by using, for example, a freezing device or cooling gas. Puncture biopsy has also been commonly performed in pathological diagnosis based on tissue sampling.

In the medical environment, it is necessary to position a needle or multiple needles precisely inside tissue or a specific organ for accurate diagnosis or minimal invasive therapy. Biopsy, ablation, cryotherapy, aspiration and drug delivery are examples that require high precision needle placement and many of these treatments require the use of multiple needles in a treatment. Prior to a percutaneous incision, a target area of interest (e.g., tumor, nodule, etc.) is confirmed by means of non-invasive imaging with MRI, ultrasound or other imaging modality. Once the target area of interest is positively determined, the clinician decides an entry point, inserting direction and depth to be reached by the needle. This process often requires a lengthy trial and error routine, which can be deleterious to the patient. Accordingly, in the last few decades there has been an increased interest in the development of needle guiding systems that can improve accuracy of needle positioning, minimize patient discomfort, and shorten time of operation.

To accurately position a needle with respect to a target, such as a tumor, in puncture treatment, an X-ray CT unit, an MRI unit, etc., for acquiring medical images is used as a visualization unit for visualizing the needle. In puncture treatment in which such a modality is used as a visualization unit, it is often difficult to position the needle with respect to the target by a single puncturing process. Thus, the needle is generally guided to the target by acquiring medical images multiple times and correcting the insertion trajectory little by little in accordance with information from the acquired images. Accordingly, to reduce the operation time and burden on patients as well as patient's exposure to imaging radiation, various needle positioning apparatuses for positioning the needle to the target to provide a reduction in the number of times of corrections of the trajectory have been developed.

For example, US2006/0229641, entitled "Guidance and Insertion System", discloses a needle positioning apparatus including a remote-center-of-motion (RCM) mechanism. According to US2006/0229641, an insertion direction is determined by driving motors, and puncturing is performed by a motor. Then, a motor is driven so as to release the needle from the needle positioning apparatus. In the case where multiple-needle puncture is performed by using this apparatus, the needle is set between a drive roller and a passive roller. If a second or additional needle is needed, the previously inserted needle is clamped between the drive roller and the passive roller and will interfere with the second or additional needle being inserted. Therefore, in multiple-needle puncture, positioning of the subsequently inserted needles cannot be performed with this apparatus.

US2006/0149147, entitled "Remotely Held Needle Guide for CT Fluoroscopy", relates to a needle positioning apparatus including a vertical articulated arm, and discloses a mechanism for releasing a needle from a needle holder by using a grip. When multiple-needle puncture is performed by using this guide apparatus, a needle can be released from a needle holder by controlling a gripping area. However, for this to occur, a main body needs to be retracted before the next insertion. More specifically, the main body needs to be carefully retracted so that the needle holder does not interfere with the needle. Thus, the vertical articulated arm is required to make a complex movement to retract the main body.

As another example of a needle positioning apparatus, Song S, Tokuda J, Tuncali K, Yamada A, Torabi M, Hata N., "Design Evaluation of a Double Ring RCM Mechanism for Robotic Needle Guidance in MRI-guided Liver Interventions", IEEE/RSJ International Conference on Intelligent Robots and Systems (IROS), Nov. 3-7, 2013, discloses a double-ring-type needle positioning apparatus, which is a two-degree-of-freedom RCM mechanism. However, an apparatus for multiple needle placements is not provided in this apparatus.

Thus, there is need for needle positioning apparatus that are suitable for, for example, minimally invasive puncture treatment and can, for example, assist in providing a more exact location of needle placement, reduce the time required to place the needle, reduce the number of punctures during a procedure, reduce the number of images required to place the needle(s), and/or aid in the placement of multiple needles during a procedure.

SUMMARY OF EXEMPLARY EMBODIMENTS

In puncture treatments such as ablation treatment and cryotherapy, multiple-needle puncture using a plurality of needles may be performed to reliably exterminate the tumor or otherwise affect the treatment area. In multiple-needle puncture, the treatment is performed while one or more needles are in the inserted state. Therefore, a needle that has already been inserted as well as the apparatus used to insert that needle may obstruct the positioning of the needle to be inserted next.

A positioning apparatus according to some embodiments of the present invention includes a needle holder having a through hole that is adapted to at least partially surround a needle to guide the needle in a longitudinal direction; a needle positioning unit having a base part adapted for mounting on a patient and a moving part having at least two degrees of freedom, which holds the needle holder and moves together with the needle holder so as to position the needle holder, and an engagement member that fixes a position of the needle holder with respect to the needle positioning unit. This can be accomplished either by the engagement member being at least partially detachably attached to the needle positioning unit or the needle holder being at least partially detachably attached to the engagement member. Thus, the positioning apparatus is able to regulate a movement direction of the needle where the needle, or needles, may be attached and detached by a physician during use.

In some embodiments, a positioning apparatus that provides for the positioning of multiple needles is described. This is particularly useful for procedures and therapies where multiple needles are required to be precisely placed at an insertion site.

There are several configurations contemplated and discussed herein by which the needle holder is attached to the engagement member. The needle holder can detach or partially detach to facilitate removal of the needle holder from the placement apparatus and thus from the physicians working area and/or release of the needle. There are several configurations contemplated, some of which are described herein below. For example, the positioning apparatus may also comprise one or more fixing members on the engagement member and/or the needle positioning unit that comprise (A) a protruding portion and the other comprises a recessed portion or hole for engaging the needle holder with the engagement member, (b) inset portions on the needle positioning unit configured to hold a portion of the engagement member, and/or (c) a hinging member and a hinge receptor for engaging the needle holder with the needle positioning unit. The engagement member comprises a key that is adapted to slideably attach to the needle positioning unit via a keyway located on the needle positioning unit.

There are several configurations contemplated by which the needle holder can hold a needle and also release a needle once the needle is placed. For example, the needle holder can retain the needle with an enclosed through-hole, a C-shaped through-hole or a U-shaped through-hole. A shutter or separable needle holder can be used to retain and then release the needle as well, where the separable needle holder may completely separate or partially separate, such as by a hinged rotation. The apparatus may also comprise a releasing mechanism adapted to release a needle via an energizing mechanism.

This invention also provides a method of placing multiple needles into an insertion location comprising: (a) securing at least part of a needle positioning apparatus over an insertion location; (b) acquiring an MR image of the insertion location, or more particularly of a target position below the insertion location; (c) specifying two or more needle target locations based on the acquired MR image; (d) optionally securing the rest of the needle positioning apparatus over the insertion location; (e) calculating insertion directions for two or more needles for insertion at the needle target locations; (f) calculating the configurations of the needle positioning apparatus based on the insertion directions, such that the movement direction of the two or more needles held by the needle positioning apparatus would be regulated to the insertion direction; (g) rotating or otherwise moving a portion of the needle positioning apparatus based on the calculated configuration for a first needle; (h) inserting the first needle; (i) releasing or removing the first needle from the needle holder; (j) optionally removing or detaching the needle holder and/or engagement member from the apparatus; (k) rotating or otherwise moving a portion of the needle positioning apparatus based on the calculations for a second needle; (l) inserting the second needle; (m) releasing or removing the second needle from the needle holder, and (n) optionally releasing or removing the second needle from the needle holder and optionally removing or detaching the needle holder and/or engagement member from the apparatus. These steps can be repeated, as appropriate, with additional needles and additional MR image acquisition.

Further features of the present invention will become apparent from the following description of exemplary embodiments with reference to the attached drawings.

BRIEF DESCRIPTION OF THE DRAWINGS

FIG. 6 is a schematic perspective view of a needle positioning apparatus.

FIG. 7(a) and FIG. 7(b) are other schematic perspective views of the needle positioning apparatus illustrated in FIG. 6.

FIG. 8 is another schematic perspective view of the needle positioning apparatus illustrated in FIG. 6.

FIG. 9 is another schematic perspective view of the needle positioning apparatus illustrated in FIG. 6.

FIG. 10(a) and FIG. 10(b) are other schematic perspective views of the needle positioning apparatus illustrated in FIG. 6.

FIG. 11 is another schematic perspective view of the needle positioning apparatus illustrated in FIG. 6.

FIG. 14(a) and FIG. 14(b) are other schematic perspective views of the needle positioning apparatus illustrated in FIG. 12.

FIG. 15 is a schematic perspective view of a needle positioning apparatus.

FIG. 16(a) and FIG. 16(b) are other schematic perspective views of the needle positioning apparatus illustrated in FIG. 15.

FIG. 17 is another schematic perspective view of the needle positioning apparatus illustrated in FIG. 15.

FIG. 18(a) and FIG. 18(b) are other schematic perspective views of the needle positioning apparatus illustrated in FIG. 15.

FIG. 19 is a schematic perspective view of a needle positioning apparatus.

FIG. 23(a) and FIG. 23(b) are other schematic perspective views of the needle positioning apparatus illustrated in FIG. 19.

FIG. 24 is a schematic perspective view of a needle positioning apparatus.

FIG. 25(a) and FIG. 25(b) are other schematic perspective views of the needle positioning apparatus illustrated in FIG. 24.

FIG. 26 is a schematic perspective view of a needle positioning apparatus.

FIG. 27(a) and FIG. 27(b) are other schematic perspective views view of the needle positioning apparatus illustrated in FIG. 26.

FIG. 28 is another schematic perspective view of the needle positioning apparatus illustrated in FIG. 26.

FIG. 29(a), FIG. 29(b), and FIG. 29(c) are other schematic perspective views of the needle positioning apparatus illustrated in FIG. 26.

FIG. 30 is a schematic perspective view of a needle positioning apparatus.

FIG. 31(a) and FIG. 31(b) are other schematic perspective views of the needle positioning apparatus illustrated in FIG. 30.

FIG. 32(a) and FIG. 32(b) are sectional perspective views of needle holders.

FIGS. 34(a)-(g) are cross-sectional views of the needle holder and needle guide.

FIG. 35(a) is a schematic perspective view of a needle holder. FIG. 35(b) is a cross-sectional view taken along axis A in FIG. 35(a).

FIG. 36(a) is a plan view of a needle holder. FIG. 36(b) is a cross-sectional view taken along line D-D in FIG. 36(a).

FIG. 37(a) and FIG. 37(b) are plan views of the needle holder illustrated in FIG. 36(a).

FIG. 39(a) top view of a needle positioning apparatus having an open ring-shaped engagement member and a needle holder.

FIG. 44(a), FIG. 44(b), and FIG. 44(c) are schematic perspective views of a needle positioning apparatus 201.

FIG. 45(a) and FIG. 45(b) are schematic perspective views of needle holders 208 and 209.

DESCRIPTION OF THE EMBODIMENTS

Figure 1:
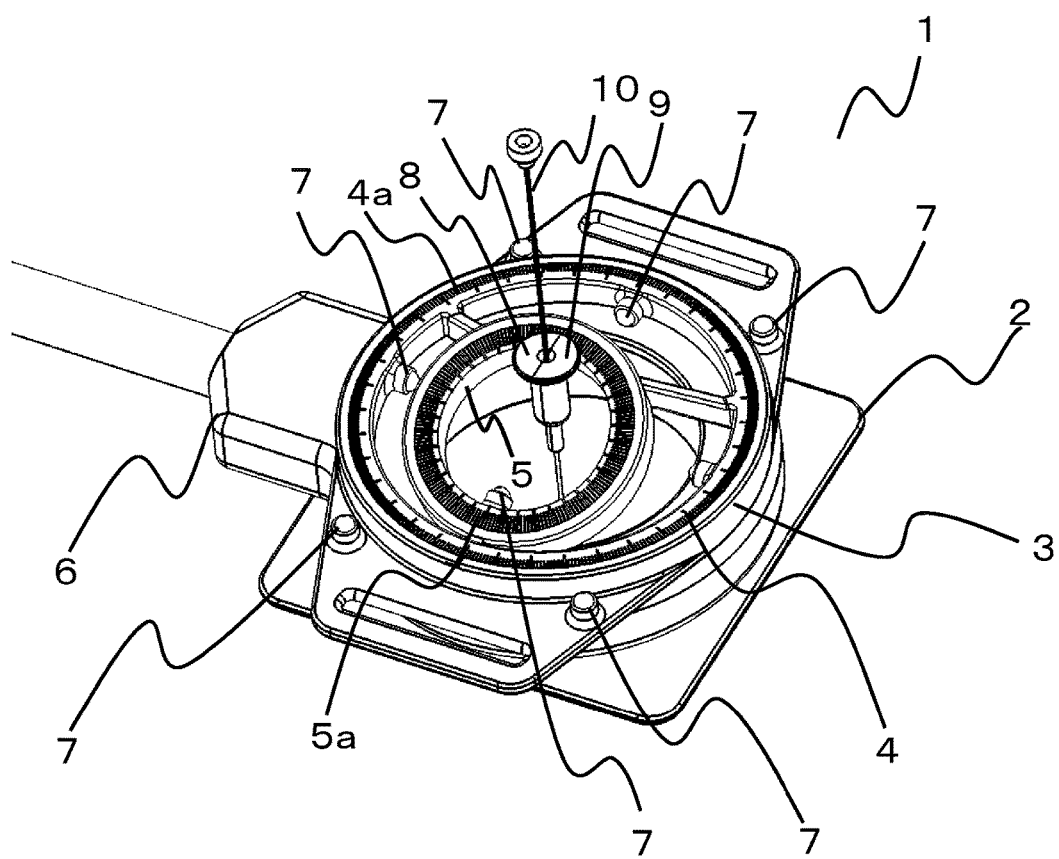
FIG. 1 is a schematic perspective view of a needle positioning apparatus.

In referring to the description, specific details are set forth in order to provide a thorough understanding of the examples disclosed. In other instances, well-known methods, procedures, components and materials have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description and/or illustration to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. The term "position" or "positioning" should be understood as including both spatial position and angular orientation.

Some embodiments of the present invention may be practiced on a computer system that includes, in general, one or a plurality of processors for processing information and instructions, RAM, for storing information and instructions, ROM, for storing static information and instructions, a data storage device such as a magnetic or optical disk and disk drive for storing information and instructions, (e.g., an MRI image) an optional user output device such as a display device (e.g., a monitor) for displaying information to the computer user, and an optional user input device.

As will be appreciated by those skilled in the art, the present examples may be embodied, at least in part, a computer program product embodied in any tangible medium of expression having computer-usable program code stored therein. For example, some embodiments described below with reference to flowchart illustrations and/or block diagrams of methods, apparatus (systems) and computer program products can be implemented by computer program instructions. The computer program instructions may be stored in computer-readable media that can direct a computer or other programmable data processing apparatus to function in a particular manner, such that the instructions stored in the computer-readable media constitute an article of manufacture including instructions and processes which implement the function/act/step specified in the flowchart and/or block diagram.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

First Embodiment

Figure 2:
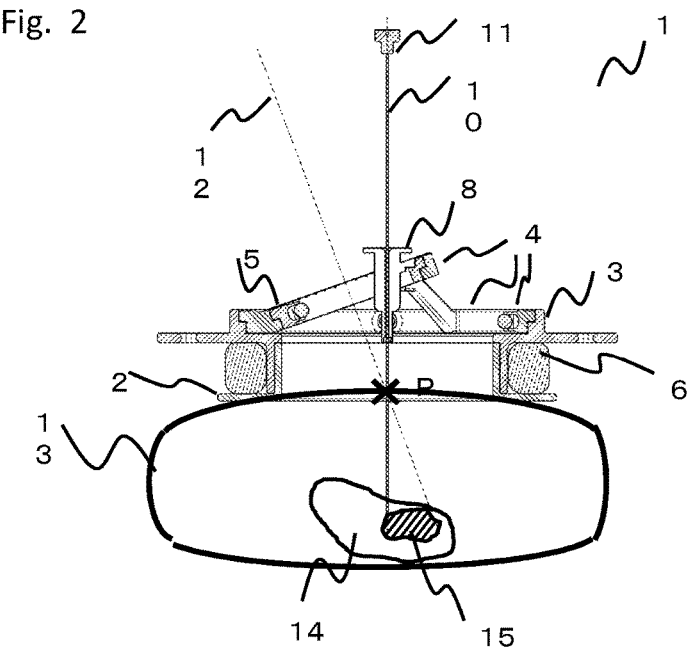
FIG. 2 is a schematic sectional view of the needle positioning apparatus illustrated in FIG. 1.
Figure 3:
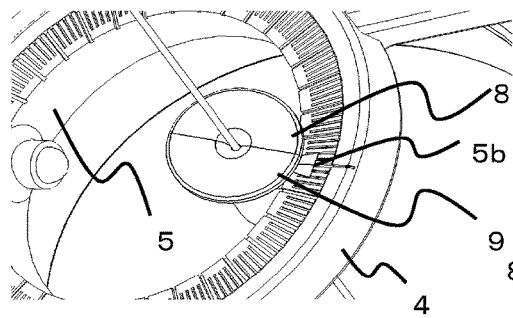
FIG. 3 is another schematic perspective view of the needle positioning apparatus illustrated in FIG. 1.
Figure 4:
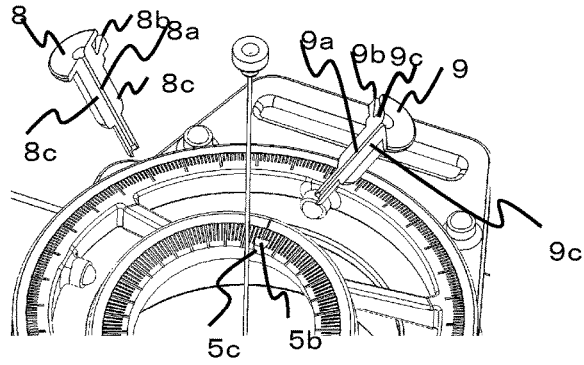
FIG. 4 is another schematic perspective view of the needle positioning apparatus illustrated in FIG. 1.

A first embodiment will now be described with reference to FIGS. 1 to 5. FIGS. 1, 3, and 4 are schematic perspective views of a needle positioning apparatus 1 according to the first embodiment. FIG. 2 is a schematic sectional view of the needle positioning apparatus 1 illustrating the manner in which puncture operation is performed by using the needle positioning apparatus 1. The needle positioning apparatus 1 according to the present embodiment is a remote-center-of-motion (RCM) mechanism having two rotational degrees of freedom. The detailed structure of the needle positioning apparatus 1 will now be described. In the present embodiment, an MRI unit is used as a visualization unit for the needle positioning apparatus 1.

Referring to the figures, the needle positioning apparatus 1 includes a mounting portion 2 which attaches to a human body 13. A base 3 is attached to the mounting portion 2. A guiding mechanism including a rail, a bearing, etc., used to move a first rotating member 4 along a specific (arc-shaped) trajectory is provided on one or each of the base 3 and the first rotating member 4. The guiding mechanism allows the first rotating member 4 to rotate around a rotation axis 11 with respect to the base 3. The first rotating member 4 includes a scale portion 4a, so that an angle thereof with respect to the base 3 can be adjusted. A second rotating member 5 is arranged so that it is not parallel to the first rotating member and is at a predetermined angle with respect to the base 3. A guiding mechanism including a rail, a bearing, etc., used to move the second rotating member 5 along a specific (arc-shaped) trajectory is provided on one or each of the first rotating member 4 and the second rotating member 5. The guiding mechanism allows the second rotating member 5 to rotate around a rotation axis 12. As described in detail below, in practice, the second rotating member 5 is rotatable along an arc-shaped trajectory while holding needle holders, and serves as a needle positioning unit that rotates so as to adjust the positions of the needle holders. When the first rotating member 4 is rotated while the position of the second rotating member 5 relative to the first rotating member 4 is fixed, the first rotating member 4 also serves as a needle positioning unit that adjusts the positions of the needle holders. The rotation axes 11 and 12 intersect at point P. The needle positioning apparatus 1 is an RCM mechanism that controls the insertion direction of the needle by a pivoting motion around point P.

A method for holding a needle will now be described. Needle holder members 8 and 9 respectively include wedge-shaped retaining portions 8b and 9b (fixing members of the needle holders) and divided portions 8c and 9c. The retaining portions 8b and 9b of the needle holder members 8 and 9, respectively, are engaged with the engagement member including a sliding portion 5b and a holding portion 5c (fixing members of the engagement member) provided on the second rotating member 5 while the divided portions 8c and 9c of the needle holder members 8 and 9, respectively, are in contact with each other, so that the needle holder members 8 and 9 are attached to the second rotating member 5. In the present embodiment, as illustrated in FIGS. 3 and 4, the engagement member has a wedge-shaped recess in a side surface thereof, and the needle holder members 8 and 9 are fitted in the recess so that they are restrained in the radial and circumferential directions. The needle holder members 8 and 9 also have semicylindrical grooves 8a and 9a which form a through hole when the divided portions 8c and 9c are in contact with each other, the through hole being capable of holding the needle in a 360-degree rotatable manner and guiding the needle in the longitudinal direction thereof. Thus, the through hole is formed by the two needle holder members 8 and 9.

Here, to hold the needle "in a 360-degree rotatable manner" means that the movement direction of the needle is restricted, more specifically, that the needle is restrained so as to have no degree of freedom in directions other than the longitudinal direction and the rotational direction around the axis. The through hole is not limited as long as this function is provided, and it is not necessary that the needle that extends through the needle holders be retained over the entire area of the side surface (entire circumference) thereof.

Instead, the needle that extends through the needle holders may be partially retained at the side surface (circumference) thereof so that the needle has no degree of freedom in directions other than the longitudinal direction and the rotational direction around the axis.

Figure 5:
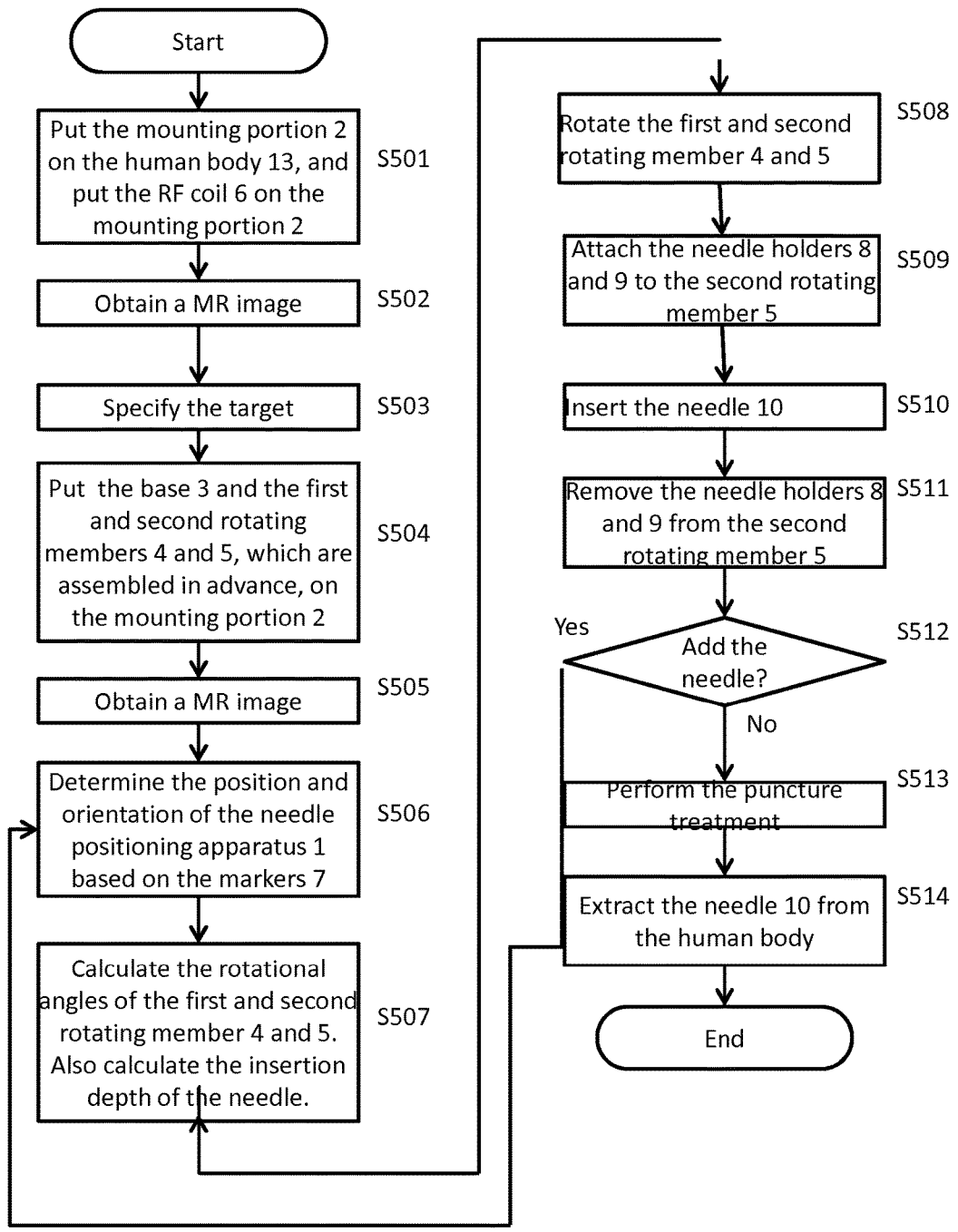
FIG. 5 illustrates a workflow of a puncture operation in which the needle positioning apparatus illustrated in FIG. 1 is used.

An exemplary workflow of puncture treatment for a target (object into which the needle is inserted), such as a tumor, will now be described. FIG. 5 illustrates the workflow. Referring to FIG. 2, the human body 13, that is, the body of a patient is placed on an MRI gantry. Here, it is assumed that the target of puncture treatment is a tumor 15 in a certain organ 14. A procedure for visualizing the target 15 by MRI will now be described.

First, a doctor secures the mounting portion 2 to the human body 13, and sets an RF coil 6 (step S501). The RF coil 6 is configured to resonate at a resonant frequency that corresponds to the intensity of a magnetic field that is used, and receives an NMR signal from the human body 13 excited by an excitation coil (not shown). The received signal does not include spatial information. Accordingly, a gradient magnetic field coil (not shown), which three-dimensionally disturbs the magnetic field, is used to acquire the spatial information, so that signals from the respective voxels can be individually detected and a single MR (slice) image can be obtained (step S502).

The doctor specifies the target, such as cancer cells or a tumor, on the basis of the acquired MR image (step S503). Then, the doctor places the base 3, the first rotating member 4, and the second rotating member 5, which are assembled in advance, on the mounting portion 2 (step S504). A MR image is taken and acquired again (step S505). Spherical markers 7 are mounted on the base 3, the first rotating member 4, and the second rotating member 5. The position and orientation of the needle positioning apparatus 1 with respect to the human body can be determined by taking an image of the needle positioning apparatus 1 including the markers 7 by MRI (step S506). To determine an insertion direction of the needle, a rotational angle of the first rotating member 4 with respect to the base 3 and a rotational angle of the second rotating member 5 with respect to the first rotating member 4 are geometrically calculated on the basis of the positional relationship between the tumor, that is, the human body, and the needle positioning apparatus 1 (step S507). The first rotating member 4 and the second rotating member 5 are rotated in accordance with the calculation results of the rotational angle of the first rotating member 4 and the rotational angle of the second rotating member 5 (step S508), and then the needle holder members 8 and 9 are attached to the second rotating member 5 (step S509).

The doctor inserts a needle 10 through the through hole 8a and 9a with the point P serving as an entry point, and into the human body to a geometrically calculated insertion depth (step S510). The needle used in the present embodiment may be a medical needle, such as a cryo-needle, an ablation-needle, or a biopsy-needle. Other needle types as well as other medical instruments are also contemplated for use in the apparatus as described herein. The diameter of the medical needle is determined by the use of the needle, and, in some embodiments, may be approximately 5 mm or less. Accordingly, to guide such a needle, the diameter of the through hole formed by the needle holder may be 5 mm or less.

When the needle 10 reaches the target 15, the needle holder members 8 and 9 are extracted along the sliding portion 5b in the longitudinal direction of the needle 10, and are removed from the second rotating member 5, as illustrated in FIG. 4 (step S511). Then, puncture treatment is performed on the target 15 (step S513). When the puncture treatment is completed, the doctor extracts the needle 10 from the human body (step S514). In the case where multiple-needle puncture is to be performed by using an additional needle(s) (step S512), the image acquisition for the measurement of the position and orientation of the needle positioning apparatus is performed again before the puncture treatment for the target 15. The workflow of the steps after that is similar to that in FIG. 5. After the needle 10 is inserted, as illustrated in FIG. 4, the needle holder members 8 and 9 are extracted along the sliding portion 5b in the longitudinal direction of the needle 10, and are detached (separated) from each other. Thus, the needle holder members 8 and 9 can be released from the needle positioning apparatus 1. Since the needle holder members 8 and 9 are configured so that they can be detached (separated) from each other, an opening that extends in the longitudinal direction of the needle is formed as a through hole, and the needle is released through this opening. When the width of the opening in a direction perpendicular to the longitudinal direction of the needle is Wo and the width of the needle in the direction perpendicular to the longitudinal direction of the needle is Wn, Wo needs to be larger than or equal to Wn to allow the needle to be released.

The workflow of FIG. 5 briefly illustrates a simulative operation method, but the workflow is not limited to this operation method. This exemplary workflow may also apply to the following embodiments.

One advantageous feature of the present invention, as described in this embodiment and several others is the detachable needle holder. In this embodiment, the two needle holder members 8 and 9 can be detached from the needle positioning apparatus. Thus, prior to operation of the needle positioning apparatus, the needle holders (and needles) can be provided as sterilized articles. In contrast, the needle positioning unit portion of the apparatus does not necessarily need to be sterilized and can be placed outside of the sterile field during operation. Thus, this simplifies the procedure where sterilization is required and can reduce both time requirements and cost.

According to present embodiments, the needle can be released from the needle positioning apparatus after the needle has been positioned. Therefore, the needle and apparatus can be prevented from damaging the body of the patient when the patient breathes or moves. In addition, when multiple-needle puncture is performed, the needle holders can be prevented from interfering with the second and the following needles to be inserted by releasing the placed needles from the needle holder. In the present embodiment, the needle holders can be removed from the needle positioning apparatus after the insertion.

In some embodiments, the needle holder and/or needle positioning apparatus are configured such that the force used to detach or at least partially detach the needle holder from the engagement member or the engagement member from the needle positioning unit occurs via a force perpendicular to the movement direction of the needle. In some embodiments, the detachment occurs via a force that is at an angle relative to the movement direction of the needle. In some other embodiments, the force used to detach or at least partially detach the needle holder from the engagement member has a force component perpendicular to the movement direction of the needle is small enough to be absorbed by the flexibility of the needle. In some embodiments, it is contemplated that the physician would hold the needle when this force is applied to minimize the movement of the part of the needle inserted into the patient. Thus, a patient with one or more needles inserted will feel less discomfort or pain that is associated with the lateral movement of an inserted needle.

In some embodiments, the needle holder and/or needle positioning apparatus are configured such that the force used to detach or at least partially detach the needle holder from the engagement member occurs via a force perpendicular to the movement direction of the needle. In some embodiments, the detachment occurs via a force that is at an angle relative to the movement direction of the needle. In some other embodiments, the force used to detach or at least partially detach the needle holder from the engagement member has a force component perpendicular to the movement direction of the needle is small enough to be absorbed by the flexibility of the needle.

In some embodiments, the needle holders can be formed as, for example, disposable components made of an inexpensive resin material. When the needle holders are disposable, it is not necessary to perform a sterilization step after using them. Therefore, strict contamination control can be achieved regardless of the environment of individual medical sites. As a result, the reliability of the operation can be increased. Thus, in some embodiments the needle holder is fully detachable from the engagement member and can be combined with the positioning apparatus for use after sterilization of the needle holder.

The needle positioning unit as shown in this embodiment provides two rotational two degrees of freedom for positioning the needle holder and thus the needle at a target incision site. These degrees of freedom may be provided by arc-shaped guide structures. In some embodiments, there are two or more rotational degrees of freedom allow for rotation around a first axis that is substantially perpendicular to the surface on which it is place and a second axes that is angled relative to the first axis. In some embodiments, the angle between the first and second axes is between 5° and 85°, or between 15° and 60°, such as 20°, 30°, 40°, or 45°. In some embodiments, at least one degree of freedom allows for the translation of the needle positioning unit (for example, it may include an X or XY translational stage.) In some embodiments as exemplified herein the at least two rotational degrees of freedom are obtained.

Moreover, with the needle positioning apparatus according to the several embodiments as described herein, after the needle is inserted, the needle holders can be quickly released from the needle positioning apparatus without moving the needle positioning apparatus and while the insertion state of the needle is maintained. Therefore, the needle holders according to the present embodiment can be used irrespective of the structure of a needle positioning unit. In other words, the present invention is not limited to the RCM mechanism having two rotational degrees of freedom described herein.

In the present embodiment, no driving unit for the first and second rotating members is specified. The first and second rotating members may either be driven manually or by a driving unit including a motor. Similarly, a motor for inserting the needle in the longitudinal direction may be provided. In the case where an MRI unit is used as a visualization unit as in the present embodiment, a driving unit including an ultrasonic motor composed of a non magnetic material may be used; however, the present invention is not limited to this.

In the present embodiment, an MRI unit is used as a visualization unit for the needle and a position-and-orientation measurement unit for the needle positioning apparatus. Therefore, a nonmagnetic metal, a resin, a ceramic, etc., are suitable as a material of the needle positioning apparatus. However, the visualization and position-and-orientation measurement unit is not limited, and an X-ray CT unit, for example, may instead be used. A material suitable for the selected visualization and position-and-orientation measurement unit may be used as a material of the needle positioning apparatus.

These modifications may also be applied to the following embodiments.

Second Embodiment

A second embodiment will now be described with reference to FIGS. 6 to 11. Components similar to those of the first embodiment are denoted by the same reference numerals, and descriptions thereof are thus omitted. FIG. 6 is a schematic perspective view of a needle positioning apparatus 21 according to the second embodiment.

Needle holders, which are needle holding units, will now be described in detail with reference to the drawings. Similar to the first embodiment, a second rotating member 25, which is rotatable relative to a first rotating member 4, is provided on the first rotating member 4. As illustrated in schematic perspective views of FIGS. 7 and 8, needle holder members 28 and 29, which are needle holding units, are provided on the second rotating member 25. The needle holder members 28 and 29 respectively include semicylindrical retaining portions 28b and 29b (fixing members of the needle holders) and divided portions 28c and 29c. A sliding portion 25b (fixing member of the engagement member), which is a cylindrical hole that is parallel to the longitudinal direction of a needle, is formed in a top surface of the second rotating member 25, and a holding portion 25c, which is an oblique surface that is parallel to the longitudinal direction of the needle, is formed on a side surface of the second rotating member 25. A cylindrical shape is formed when the divided portions 28c and 29c of the needle holder members 28 and 29, respectively, are in contact with each other and the retaining portions 28b and 29b of the needle holder members 28 and 29, respectively, are in contact with each other. The needle holders are engaged with the engagement member including the sliding portion 25b provided on the second rotating member 25, so that the needle holders are attached to the second rotating member 25. As illustrated in FIG. 8, the holding portion 25c provided on a side surface of the second rotating member 25 is configured to restrict the positions of the needle holder members 28 and 29 in the rotational direction around the central axis of the sliding portion 25b. The needle holder members 28 and 29 form a through hole 28a and 29a capable of holding the needle in a 360-degree rotatable manner and guiding the needle in the longitudinal direction.

An example of the present embodiment other than the example illustrated in FIGS. 7 to 9 will be described with reference to FIGS. 10 and 11.

FIGS. 10 and 11 are schematic sectional views of a needle positioning apparatus. A second rotating member 25, which is rotatable relative to a first rotating member 4, is provided on the first rotating member 4. As illustrated in FIGS. 10 and 11, needle holder members 28 and 29, which are needle holding units, are provided on the second rotating member 25. The needle holder members 28 and 29 respectively include cylindrical retaining portions 28b and 29b and divided portions 28c and 29c. Two sliding portions 25b (fixing members of the engagement member), which are cylindrical holes that are parallel to the longitudinal direction of a needle, are formed in a top surface of the second rotating member 25, and a holding portion 25c, which is an oblique surface that is parallel to the longitudinal direction of the needle, is formed on a side surface of the second rotating member 25. The retaining portions 28b and 29b of the needle holder members 28 and 29 (fixing members of the needle holders) are engaged with the engagement member including the sliding portions 25b provided on the second rotating member 25 while the divided portions 28c and 29c of the needle holder members 28 and 29, respectively, are in contact with each other, so that the needle holder members 28 and 29 are attached to the second rotating member 25. As illustrated in FIG. 11, the holding portion 25c provided on a side surface of the second rotating member 25 is configured to restrict the positions of the needle holders and in the rotational direction around the central axes of the sliding portions 25b. The needle holder members 28 and 29 form a through hole 28a and 29a capable of holding the needle in a 360-degree rotatable manner and guiding the needle in the longitudinal direction.

The detailed workflow of puncture treatment for a target, such as a tumor, in which an MRI unit is used as a visualization unit, is similar to that in the first embodiment, and descriptions thereof are thus omitted. In the present embodiment, similar to the first embodiment, when multiple-needle puncture is performed, steps similar to those illustrated in FIG. 5 are performed. After the needle is inserted, the needle holders are extracted along the sliding portions in the longitudinal direction of the needle, as illustrated in FIGS. 9 and 11, so that the needle holders can be released from the needle positioning apparatus.

Third Embodiment

Figure 12:
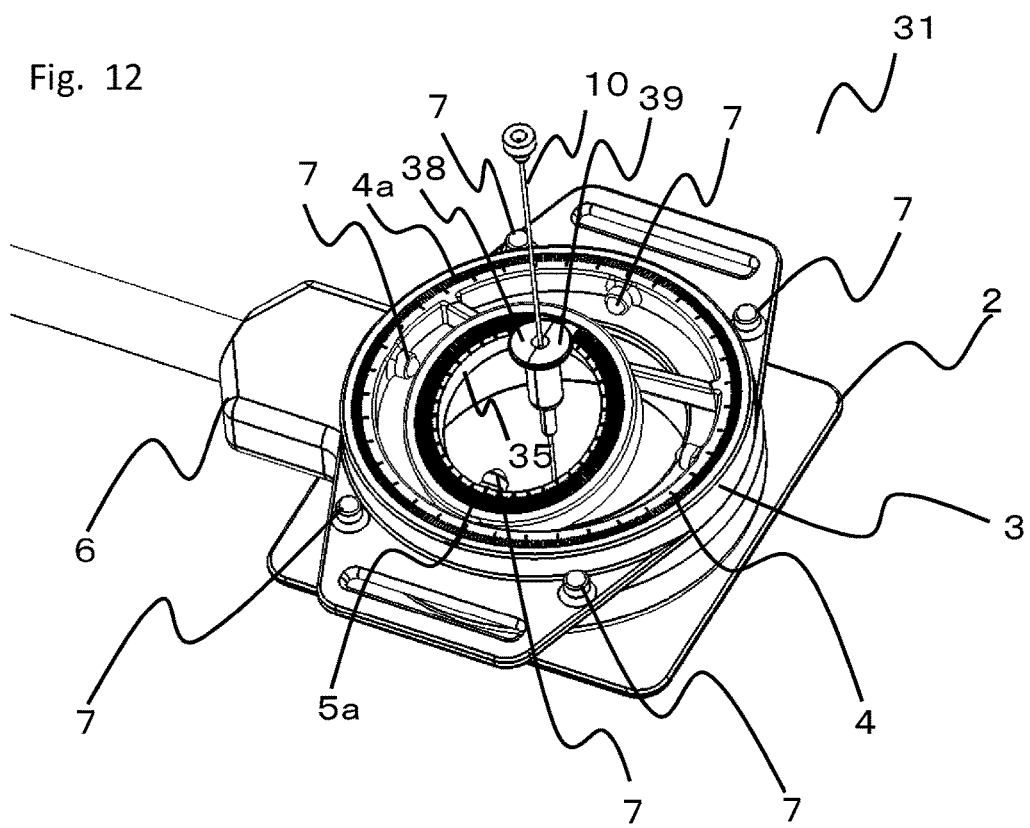
FIG. 12 is a schematic perspective view of a needle positioning apparatus.
Figure 13A:
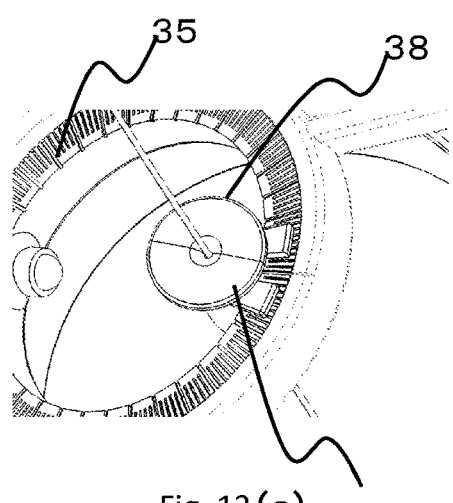
FIG. 13(a) and FIG. 13(b) are other schematic perspective views of the needle positioning apparatus illustrated in FIG. 12.

A third embodiment will now be described with reference to FIGS. 12 to 14. Components similar to those of the above-described embodiments are denoted by the same reference numerals, and descriptions thereof are thus omitted. FIG. 12 is a schematic perspective view of a needle positioning apparatus 31 according to the third embodiment.

Figure 13B:
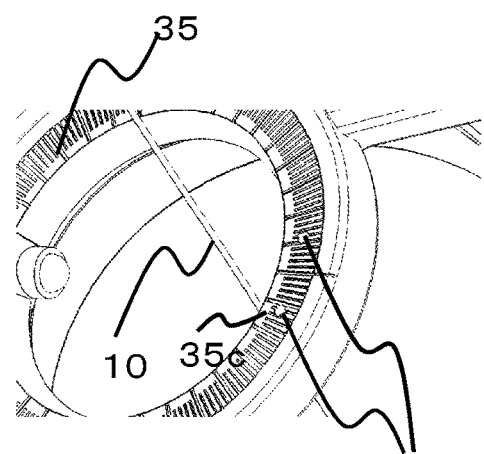
Figures 20A, 20B:
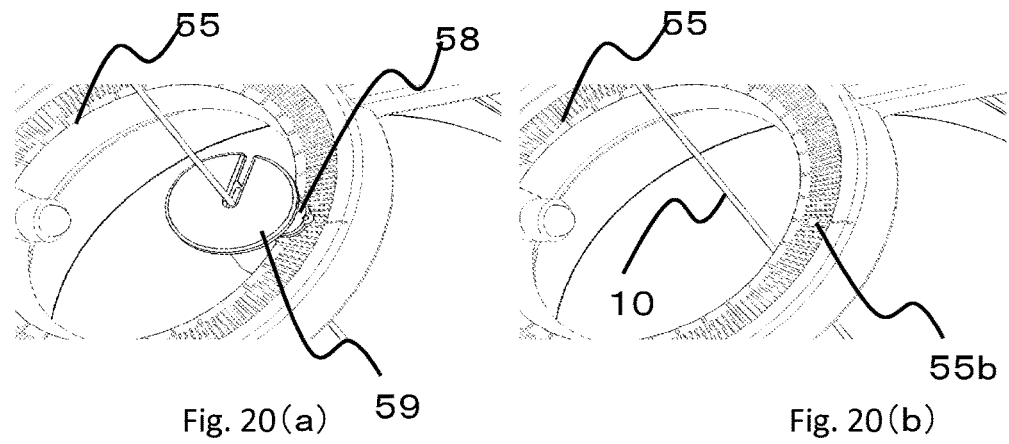
FIG. 20(a) and FIG. 20(b) are other schematic perspective views of the needle positioning apparatus illustrated in FIG. 19.

Needle holders, which are needle holding units, will now be described in detail with reference to the drawings. Similar to the first embodiment, a second rotating member 35, which is rotatable relative to a first rotating member 4, is provided on the first rotating member 4. As illustrated in schematic perspective views of FIGS. 12 and 13, needle holder members 38 and 39, which are needle holding units, are provided on the second rotating member 35. The needle holder members 38 and 39 respectively include cylindrical retaining portions 38b and 39b (fixing members of the needle holders) and divided portions 38c and 39c. A sliding portion 35b (fixing member of the engagement member), which is a cylindrical hole that is not parallel to the longitudinal direction of a needle, is formed in a top surface of the second rotating member 35. The retaining portions 38b and 39b of the needle holder members 38 and 39, respectively, are engaged with the engagement member including the sliding portion 35b provided on the second rotating member 35 while the divided portions 38c and 39c of the needle holder members 38 and 39, respectively, are in contact with each other, so that the needle holder members 38 and 39 are attached to the second rotating member 35. In the second embodiment, as illustrated in FIG. 8, an oblique surface provided on an inner side surface of the second rotating member 25 functions as the holding portion 25c. In the present embodiment, as illustrated in FIG. 13(b), an inner side surface of the second rotating member may be formed as a cylindrical surface, and is not necessarily an oblique surface as in the second embodiment. The top end surface of the second rotating member 35 serves as a holding portion 35c. The needle holder members 38 and 39 form a through hole 38a and 39a capable of holding the needle in a 360-degree rotatable manner and guiding the needle in the longitudinal direction. A restraining unit (not shown) may be provided to restrain the needle holder members 38 and 39 relative to each other when the needle holder members 38 and 39 are engaged with the second rotating member 35.

The detailed workflow of puncture treatment for a target, such as a tumor, in which an MRI unit is used as a visualization unit, is similar to that in the first embodiment, and descriptions thereof are thus omitted. In the present embodiment, similar to the first embodiment, when multiple-needle puncture is performed, steps similar to those illustrated in FIG. 5 are performed. A method for releasing the needle holders after the needle is inserted will now be described.

First, as illustrated in FIG. 14(a), the needle holder members 38 and 39 are rotated around the axis of the sliding portion 35b in a direction away from the needle. Next, the needle is extracted from the needle positioning apparatus in the direction of central axis of the sliding portion, so that the needle holder members 38 and 39 are released from the needle positioning apparatus.

As illustrated in FIG. 14, a method for releasing the needle holder according to the present embodiment includes two steps. As illustrated in FIG. 14(a), first, a needle holder member is moved away from the needle in the radial direction of the needle, so that the risk of interference between the needle and the needle holders can be reduced when the needle holder is released (or multiple needles holders are released). Therefore, not only can the effects described in the first and second embodiments be achieved, but the safety can be increased.

Fourth Embodiment

A fourth embodiment will now be described with reference to FIGS. 15 to 18. Components similar to those of the above-described embodiments are denoted by the same reference numerals, and descriptions thereof are thus omitted. FIG. 15 is a schematic perspective view of a needle positioning apparatus 41 according to the fourth embodiment.

Needle holders, which are needle holding units, will now be described in detail with reference to the drawings. Similar to the first embodiment, a second rotating member 45, which is rotatable relative to a first rotating member 4, is provided on the first rotating member 4. As illustrated in the schematic perspective view, needle holder members 48 and 49, which are needle holding units, are provided on the second rotating member 45. The needle holder members 48 and 49 include hinge-shaped connecting portions 48d and 49d, and are connected to each other by the connecting portions 48d and 49d such that they are rotatable in a rotational direction of the hinge.

The needle holder 48 includes a cylindrical retaining portion 48b. The needle holder members 48 and 49 include divided portions 48c and 49c, respectively. A sliding portion 45b (fixing member of the engagement member), which is a cylindrical hole that is parallel to the longitudinal direction of a needle, is formed in a top surface of the second rotating member 45. A holding portion 45c, which is an oblique surface that is parallel to the longitudinal direction of the needle, is formed on a side surface of the second rotating member 45. The retaining portion 48b of the needle holder 48 (fixing member of the needle holder) is engaged with the engagement member including the sliding portion 45b provided on the second rotating member 45 while the divided portions 48c and 49c of the needle holder members 48 and 49, respectively, are in contact with each other, so that the needle holder members 48 and 49 are attached to the second rotating member 45. As illustrated in FIG. 17, the holding portion 45c provided on a side surface of the second rotating member is configured to restrict the positions of the needle holders in the rotational direction around the central axis of the sliding portion 45b. The needle holder members 48 and 49 form a through hole 48a and 49a capable of holding the needle in a 360-degree rotatable manner and guiding the needle in the longitudinal direction. A restraining unit (not shown) is provided to restrain the needle holder members 48 and 49 relative to each other when the needle holder members 48 and 49 are engaged with the second rotating member 45.

The detailed workflow of puncture treatment for a target, such as a tumor, in which an MRI unit is used as a visualization unit, is similar to that in the first embodiment, and descriptions thereof are thus omitted. In the present embodiment, similar to the first embodiment, when multiple-needle puncture is performed, steps similar to those illustrated in FIG. 5 are performed. A method for releasing the needle holders after the needle is inserted will now be described.

First, as illustrated in FIG. 18(a), the needle holder 49 is rotated in a direction away from the needle around the rotation axis of the hinge, that is, the connecting portions. As a result of the rotation, the regulation of the movement direction of the needle 10 is stopped. After that, the needle holder members 48 and 49 are pulled along the sliding portion 45b in the longitudinal direction of the needle, so that the entire bodies of the needle holders can be released from the needle positioning apparatus. Thus, the two needle holder members (48 and 49) are not completely separated from each other, but are partially separated from each other. Also in this case, the needle holders can be configured such that an opening for releasing the needle 10 is formed in the through hole.

As illustrated in FIG. 18, a method for releasing the needle holder according to the present embodiment includes two steps. As illustrated in FIG. 18(a), first, the needle holder 49 is moved away from the needle in the radial direction of the needle, so that the risk of interference between the needle 10 and the needle holder members 48 and 49 can be reduced when the needle holder is released. Therefore, not only can the effects described in the first and second embodiments be achieved, but the safety can be increased. In addition, in the present embodiment, since two needle holder members 48 and 49, which are constituent elements, are connected to each other by the connecting portions 48d and 49d, the number of components can be reduced and the risk that a component will be lost during the operation can be reduced.

Fifth Embodiment

A fifth embodiment will now be described with reference to FIGS. 19 to 23. Components similar to those of the above-described embodiments are denoted by the same reference numerals, and descriptions thereof are thus omitted. FIG. 19 is a schematic perspective view of a needle positioning apparatus 51 according to the fifth embodiment.

Figure 21:
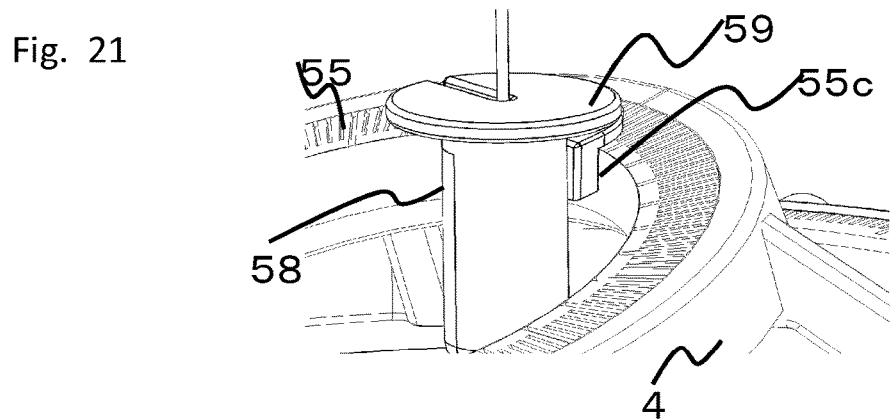
FIG. 21 is another schematic perspective view of the needle positioning apparatus illustrated in FIG. 19.
Figures 22A, 22B:
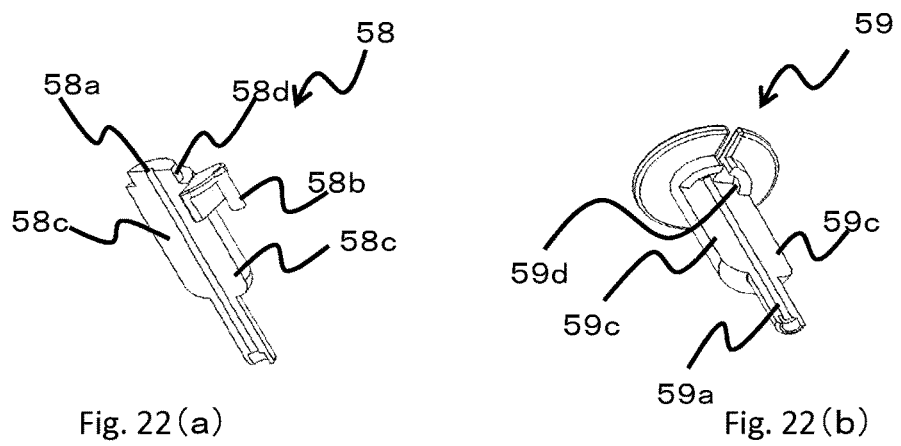
FIG. 22(a) and FIG. 22(b) are other schematic perspective views of needle holders.

Needle holders, which are needle holding units, will now be described in detail with reference to the drawings. Similar to the first embodiment, a second rotating member 55, which is rotatable relative to a first rotating member 4, is provided on the first rotating member 4. As illustrated in the schematic perspective view, needle holder members 58 and 59, which are needle holding units, are provided on the second rotating member 55. As illustrated in FIG. 22, the needle holder members 58 and 59 respectively include a fitting portion (projecting portion) 58d and a fitting portion (recessed portion) 59d, which are fitted to each other. The needle holder members 58 and 59 have a translational degree of freedom in the longitudinal direction thereof, and are therefore slidable in the longitudinal direction of the needle. The needle holder 58 includes a cylindrical retaining portion 58b (fixing member of the needle holder). The needle holder members 58 and 59 include divided portions 58c and 59c, respectively. A sliding portion 55b (fixing member of the engagement member), which is a cylindrical hole that is parallel to the longitudinal direction of a needle, is formed in a top surface of the second rotating member 55. A holding portion 55c, which is an oblique surface that is parallel to the longitudinal direction of the needle, is formed on a side surface of the second rotating member 55. The retaining portion 58b of the needle holder 58 is engaged with the engagement member including the sliding portion 55b provided on the second rotating member 55 while the divided portions 58c and 59c of the needle holder members 58 and 59, respectively, are in contact with each other, so that the needle holder members 58 and 59 are attached to the second rotating member 55. As illustrated in FIG. 21, the holding portion 55c provided on a side surface of the second rotating member is configured to restrict the positions of the needle holders in the rotational direction around the central axis of the sliding portion 55b. The needle holder members 58 and 59 form a through hole 58a and 59a capable of holding the needle in a 360-degree rotatable manner and guiding the needle in the longitudinal direction.

The detailed workflow of puncture treatment for a target, such as a tumor, in which an MRI unit is used as a visualization unit, is similar to that in the first embodiment, and descriptions thereof are thus omitted. In the present embodiment, similar to the first embodiment, when multiple-needle puncture is performed, steps similar to those illustrated in FIG. 5 are performed. A method for releasing the needle holders after the needle is inserted will now be described.

First, as illustrated in FIG. 23(a), the needle holder 59 is slid along the fitting portions, which are the connecting portions, in the longitudinal direction of the needle so that the needle holder 59 is released from the needle holder 58. After that, as illustrated in FIG. 23(b), the needle holder 58 is extracted along the sliding portion 55b in the longitudinal direction of the needle 10, so that the entire bodies of the needle holders can be released from the needle positioning apparatus.

As illustrated in FIG. 23, a method for releasing the needle holder according to the present embodiment includes two steps. As illustrated in FIG. 23(a), first, a needle holder member is moved away from the needle in the radial direction of the needle, so that the risk of interference between the needle and the needle holders can be reduced when the needle holder is released. Therefore, not only can the effects described in the first and second embodiments be achieved, but the safety can be increased.

Sixth Embodiment

A sixth embodiment will now be described with reference to FIGS. 24 and 25. Components similar to those of the first embodiment are denoted by the same reference numerals, and descriptions thereof are thus omitted. FIG. 24 is a schematic perspective view of a needle positioning apparatus 61 according to the sixth embodiment.

A needle holder, which is a needle holding unit, will now be described in detail with reference to the drawings. Similar to the first embodiment, a second rotating member 65, which is rotatable relative to a first rotating member 4, is provided on the first rotating member 4. As illustrated in the schematic perspective view, a needle holder 68, which is a needle holding unit, is provided on the second rotating member 65.

The needle holder according to the present embodiment is made of a soft material, such as silicone rubber. Although two parts are provided as detachable (separable) needle holders for forming an opening in the above-described embodiments, these parts are integrated together in the present embodiment. The needle holder 68 includes a cylindrical retaining portion 68b (fixing member of the needle holder) and a divided portion 68c. A sliding portion 65b (fixing member of the engagement member), which is a cylindrical hole that is parallel to the longitudinal direction of a needle, is formed in a top surface of the second rotating member 65. A holding portion 65c, which is an oblique surface that is parallel to the longitudinal direction of the needle, is formed on a side surface of the second rotating member 65. The retaining portion 68b of the needle holder 68 is engaged with the engagement member including the sliding portion 65b provided on the second rotating member 65, so that the needle holder 68 is attached to the second rotating member 65. As illustrated in FIG. 25, the holding portion 65c provided on a side surface of the second rotating member is configured to restrict the position of the needle holder in the rotational direction around the central axis of the sliding portion 65b. The needle holder 68 has a through-hole 68a, which are capable of holding the needle in a 360-degree rotatable manner and guiding the needle in the longitudinal direction.

The detailed workflow of puncture treatment for a target, such as a tumor, in which an MRI unit is used as a visualization unit, is similar to that in the first embodiment, and descriptions thereof are thus omitted. In the present embodiment, similar to the first embodiment, when multiple-needle puncture is performed, steps similar to those illustrated in FIG. 5 are performed.

After the needle is inserted, first, as illustrated in FIG. 25(a), a force is applied to the divided portion 68c in a direction shown by the arrow with the broken line in FIG. 25(a), so that the divided portion 68c of the needle holder 68 is deformed such that the diameter thereof becomes greater than that of the needle. Then, as illustrated in FIG. 25(b), the needle holder is extracted along the sliding portion in the longitudinal direction of the needle, so that the needle holder can be released from the needle positioning apparatus. Thus, when the divided portion 68c of the needle holder 68 is deformed, the opening that extends in the longitudinal direction of the needle is formed into a through hole. FIG. 25(a) shows the divided portion 68c in a non-deformed state, which may comprise a narrow slit extending from the through hole to the outside of the needle holder. The narrow slit may widen to form a wider slit that allows the needle to be removed from the needle holder 68 in the deformed state. Similar to the above-described embodiments, when the width of the opening in a direction perpendicular to the longitudinal direction of the needle is Wo and the width of the needle in the direction perpendicular to the longitudinal direction of the needle is Wn, Wo needs to be larger than or equal to Wn to allow the needle to be released in the deformed or divided state.

Also in the present embodiment, the effects described in the first and second embodiments can be achieved. In addition, since a single constituent element is provided as the needle holder 68 in the present embodiment, the needle holder 68 can be manufactured as a single component at a low cost by, for example, injection molding. Moreover, the needle holder, which is a single component, does not require an assembly process as in the fourth embodiment in which the needle holder members 48 and 49 having the connecting portions are assembled together, and therefore the manufacturing cost can be reduced. Furthermore, similar to the fourth embodiment, since the number of components of the needle holder is reduced, the risk that a component will be lost during the operation can be reduced.

In the present embodiment, the entire body of the needle holder is formed of silicone rubber. However, the present invention also includes a structure in which the retaining portion 68b and a portion in which the through hole 68a is formed are made of a material having a high rigidity to increase the positioning accuracy of the needle, and in which only a portion that needs to be greatly deformed to increase the divided portion 68c is made of a soft material.

Seventh Embodiment

A seventh embodiment will now be described with reference to FIGS. 26 to 29. Components similar to those of the above-described embodiments are denoted by the same reference numerals, and descriptions thereof are thus omitted. FIG. 26 is a schematic perspective view of a needle positioning apparatus 71 according to the seventh embodiment.

Needle holders, which are needle holding units, will now be described in detail with reference to the drawings. Similar to the first embodiment, a second rotating member 75, which is rotatable relative to a first rotating member 4, is provided on the first rotating member 4. As illustrated in the schematic perspective view, needle holder members 78 and 79, which are needle holding units, are provided on the second rotating member 75. The needle holder members 78 and 79 respectively include cylindrical retaining portions 78b and 79b (fixing members of the needle holders), divided portions 78c and 79c, and rotating portions 78d and 79d, which are components of a hinge. Referring to the figure, the needle holder members 78 and 79 are configured to rotate around the rotating portions 78d and 79d, which serve as rotating shafts. However, the structure of the needle holder members 78 and 79 is not limited to this. For example, a ball joint may be used in place of the rotating shafts.

A sliding portion 75b, which is a cylindrical hole, is formed in a top surface of the second rotating member 75. The divided portions 78c and 79c of the needle holder members 78 and 79, respectively, are brought into contact with each other, and the retaining portions 78b and 79b of the needle holder members 78 and 79, respectively, are engaged with the engagement member including the sliding portion 75b provided on the second rotating member 75 (fixing member of the engagement member), so that the needle holder members 78 and 79 are attached to the second rotating member 75.

As illustrated in FIG. 28, a top end surface 75c of the second rotating member 75 serves as a holding portion for holding the needle holders. The needle holder members 78 and 79 form a through hole 78a and 79a capable of holding the needle in a 360-degree rotatable manner and guiding the needle in the longitudinal direction. A restraining unit (not shown) is provided to restrain the needle holder members 78 and 79 relative to each other when the needle holders are engaged with the second rotating member.

The detailed workflow of puncture treatment for a target, such as a tumor, in which an MRI unit is used as a visualization unit, is similar to that in the first embodiment, and descriptions thereof are thus omitted. In the present embodiment, similar to the first embodiment, when multiple-needle puncture is performed, steps similar to those illustrated in FIG. 5 are performed. A method for releasing the needle holders after the needle is inserted will now be described.

First, as illustrated in FIG. 29(*a*), the needle holders are rotated around the axis of the sliding portion in a direction away from the needle. Next, as illustrated in FIG. 29(*b*), the rotating portions 78*d* and 79*d* are rotated to move the needle holder members 78 and 79 away from the needle positioning apparatus. Thus, the needle holders can be released after the needle is inserted. Similar to the above-described embodiments, as illustrated in FIG. 29(*c*), the needle holders can be released by removing the entire bodies of the needle holders from the needle positioning apparatus as necessary.

As in the method for releasing the needle holders according to the present embodiment illustrated in FIG. 29, instead of completely removing the needle holders from the needle positioning apparatus, the needle holders may be temporarily retracted as illustrated in FIG. 29(*b*). In such a case, not only can the effects described in the first and second embodiments be achieved, but the risk that the needle holders will be lost after being released can be reduced. In addition, since the needle holders are moved away from the needle in the radial direction of the needle first as illustrated in FIG. 29(*a*), the risk of interference between the needle and the needle holders can be reduced when the needle holder is released, and the safety can be increased.

In the present embodiment, the rotating portions 78*d* and 79*d*, which are components of a hinge, are used as retracting units for temporarily retracting the needle holders, as illustrated in FIG. 29(*b*). However, the retracting units are not limited to this, and any units that can be temporarily restrained with respect to the needle positioning apparatus may be used. For example, the needle holders may be connected to the needle positioning apparatus with strings.

Eighth Embodiment

An eighth embodiment according to the present invention will now be described with reference to FIGS. 30 to 32. Components similar to those of the above-described embodiments are denoted by the same reference numerals, and descriptions thereof are thus omitted. FIG. 30 is a schematic perspective view of a needle positioning apparatus 81 according to the eighth embodiment.

Needle holders, which are needle holding units, will now be described in detail with reference to the drawings. Similar to the first embodiment, a second rotating member 85, which is rotatable relative to a first rotating member 4, is provided on the first rotating member. As illustrated in the schematic perspective view, needle holder members 88 and 89, which are needle holding units, are provided on the second rotating member 85. As illustrated in FIG. 32, the needle holder members 88 and 89 include divided portions 88*c* and 89*c*, respectively, and connecting portions 88*d*, 88*e*, 89*d*, and 89*e* (shaded parts) composed of magnets are provided on the divided portions 88*c* and 89*c*. The connecting portions 88*d* and 89*d* are connected to each other by the magnets, and the connecting portions 88*e* and 89*e* are connected to each other by the magnets. Retaining portions 88*b* and 89*b* (shaded parts) composed of pieces of hook-and-loop fastener are provided on side surfaces of the needle holder members 88 and 89, respectively. As illustrated in FIG. 31(*b*), a holding portion 85*b* (shaded part) composed of a piece of hook-and-loop fastener is provided on an inner side surface of the second rotating member 85. The retaining portions 88*b* and 89*b* (fixing members of the needle holders) can be bonded to the holding portion 85*b* (fixing member of the engagement member) by the pieces of hook-and-loop fastener, so that the needle holders are fixed to the second rotating member 85. The needle holder members 88 and 89 form a through hole 88*a* and 89*a* capable of holding the needle in a 360-degree rotatable manner and guiding the needle in the longitudinal direction.

The detailed workflow of puncture treatment for a target, such as a tumor, in which an MRI unit is used as a visualization unit, is similar to that in the first embodiment, and descriptions thereof are thus omitted. In the present embodiment, similar to the first embodiment, when multiple-needle puncture is performed, steps similar to those illustrated in FIG. 5 are performed.

A method for releasing the needle holders after the needle is inserted will now be described. The needle holder members 88 and 89 are slid in the longitudinal direction of the needle while removing the retaining portions 88*b* and 89*b* from the holding portion 85*b*, and then the connecting portions are separated from each other, so that the needle holders can be released from the needle. Thus, the entire bodies of the needle holders can be released from the needle positioning apparatus. Alternatively, the retaining portions may be removed from the holding portion while separating the connecting portions from each other. According to the present embodiment, even when it is difficult to provide a physical fitting unit on the second rotating member or the needle holders, the needle holders can be easily fixed to the needle positioning apparatus. In addition, since the connecting portions 88*d*, 88*e*, 89*d*, and 89*e* are used to restrain the two needle holder members with respect to each other, the positioning accuracy of the through hole 88*a* and 89*a* can be increased.

In the present embodiment, the connecting portions 88*d*, 88*e*, 89*d*, and 89*e* are composed of as magnets, and the retaining portions 88*b* and 89*b* and the holding portion 85*b* are composed of pieces of hook-and-loop fastener. Alternatively, however, the connecting portions 88*d*, 88*e*, 89*d*, and 89*e* may be composed of pieces of hook-and-loop fastener, and the retaining portions 88*b* and 89*b* and the holding portion 85*b* may be composed of magnets. The present invention is not limited to the pieces of hook-and-loop fastener and magnets, and may include any combination of connectors, including pieces of double-sided tape, adhesive, mechanical fitting units, or combinations thereof. The connecting portions, the holding portion, and the retaining portions may have marks so that the accuracy of positioning the connecting portions with respect to each other and the accuracy of positioning the retaining portions with respect to the holding portion can be increased. The structure described in the present embodiment may also be applied to the holders according to, for example, the first to fourth, sixth, and seventh embodiments.

Needle Holders

Other forms needle holders and needle holder members may be used in place of the needle holders as described above and below. For example, the needle holder may have one of four exemplary types of configuration for release. The first example is detached needle holder. FIG. 9 shows such embodiment of completely detached needle holder, where the needle holder member(s) comes off from the rotary guide when it releases the needle. The second type is a non-detached needle holder. FIG. 18(a) shows such an embodiment where, when one needle holder member 49 opens and releases the needle, the needle holder member 48 still stays intact with the rotary guide and this is partially detachable. When moving the rotary ring for the next needle guiding or for freeing the needle allowing the patient to move, the rotary guide need to rotate in one direction so that the attached member of needle holder is not to interfering with the already inserted needle. The third type is a partly detached needle holder. FIG. 23(a) in its figure shows such an embodiment where the needle holder member 59 is removed and releases the needle; another member of the needle holder, 58 is still connected to the rotary guide. Again, similar to the second non-detached needle holder, when the next needle is to be used, the rotary guide must only move in the direction where the connected member of the needle holder is not to interfere with the already inserted needle. The fourth type is a retractable holder. The needle holder shown in FIG. 29(a) may be designed to be retractable. The needle holder after it releases by opening into two pieces, it will flip out of the guide ring inner space. This will mitigate the needle holder to interfere with the existing needle when the holder is moved to the next position for next needle guiding.

Any of these four configurations, other configurations, or combinations thereof (i.e. for devices with multiple needle holders) may be used, dependent upon the proposed configuration and use.

Particular advantages of the detached needle holder include a wide, clear space for viewing the patient and the needle insertion position and the lack of mechanical interference with existing needle. Particular advantages of the non-detached needle holder include the fact that holder piece will not fall into the ring or out of physician's hands upon release, there are fewer pieces that need to be handled and an easy release mechanism for the physician. However, mechanical interference is more likely unless the rotary guide is only moved in one direction. Particular advantages of the partially-detached needle holder include the fact that the holder piece will not fall into the ring or out of the physician's hands. Potential mechanical interferences with this type of needle holder can be reduced by only moving the rotary guide in one direction. This configuration also has one piece that can potentially fall into the ring or out of the physician's hands during use. Particular advantages of the retractable needle holder include the fact that there are no pieces of the holder that would fall during use since the holder does not fully detach. There are also fewer pieces to handle. This configuration also provides a clear view of the insertion site for the physician. Because the retractable needle holder will escape away from the inner space of rotary guide, it will avoid interference with the needle. However, this configuration requires a complex mechanism, such as the mechanism as shown herein, to work well.

In some embodiments, there may be an additional element between the needle and the needle holder, such as a small tube or hollow cylinder that surrounds a portion of the needle, at least part of that portion being the section of the needle held by the needle holder. This element may be integrally formed with the needle or it may be separate. In some embodiments, it is disposable and can be discarded along with the needle after use. In some embodiments, the additional element may have a square, oval, or rectangular cross section instead of round. This additional element may be hard or flexible and can be used, for example, to give the physician an additional element for gripping the needle and/or for more securely securing into the needle holder. This is particularly advantageous for when the needles are too thin for the physician to easily manipulate the needles. This element can also function as an adaptor. Thus, multiple elements may be provided where each of the hollow cylinder (or other shaped) pieces may have the same outer diameter but different inner diameters. This allows for different gauge needles to be used with the same needle holder in embodiments where the hole is sized for fitting the needle.

Ninth Embodiment

Figure 33:
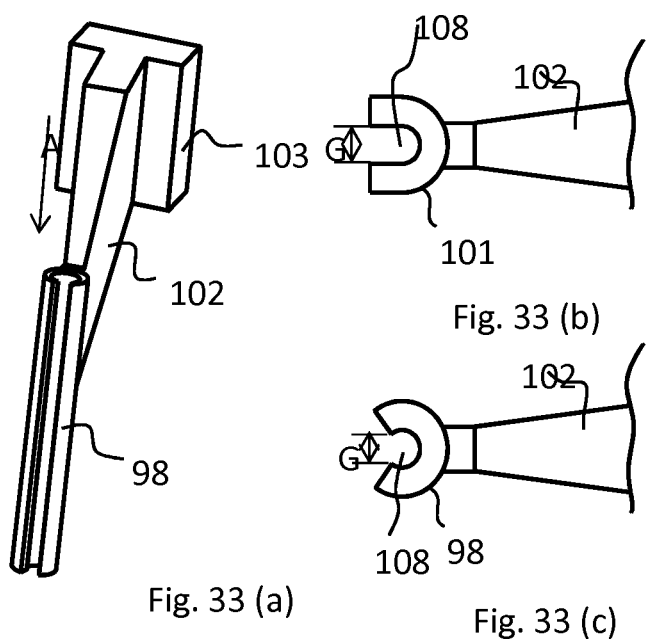
FIG. 33(a) is a schematic perspective view of a needle holder.
FIG. 33(b) and FIG. 33(c) are cross-sectional views taken along axis A in FIG. 33(a) for two embodiments.

A ninth embodiment, including several variations, will now be described with reference to FIGS. 33 to 35. FIG. 33(a) is a schematic perspective view of a needle holder including a needle guide 98 according to the ninth embodiment. The needle holders as described in this embodiment may be combined, for example, with the needle placement apparatus as described in various other embodiments or with a different needle placement apparatus. Further, the two aspects of the needle holder—the through hole that guides the needle and the attachment to the engagement member, may be separately modified based on the embodiment or aspect of the embodiment that is used to define a particular apparatus. In further detail, the needle holder includes a support member 102 and an attachment portion 103 where the attachment portion 103 attaches to the needle positioning apparatus, such as at the second rotating member (not shown) or the engagement member (also not shown). As illustrated in the two cross-sectional views along axis A (FIG. 33(b) and FIG. 33(c)), the through hole 108 in the needle guide 98 may take one of several shapes that include, but are not limited to a C-shape, a U-shape and a semi-circle. The slit width of the through hole is depicted by the parameter "G."

FIGS. 34(a)-34(g) depict exemplary embodiments of the needle guide 98 or needle guides 98 and 99 containing through hole 108 with and without a needle 10 located in the through hole 108. These figures demonstrate that, in some embodiments, the needle 10 may be released at the angle as depicted by the arrow 'a'. The embodiments of FIGS. 34(a)-34(c) and 34(g) demonstrate several deformable needle guides where the needle may be removed from the needle guide by exertion of pressure on the needle at the appropriate angle to briefly deform the needle guide and eject the needle.

In other variations, as exemplified by FIG. 35(a), a schematic perspective view of a needle holder is shown. Components similar to those of the first variation of this embodiment are denoted by the same reference numerals, and descriptions thereof are thus omitted. The needle holder includes a needle guide 98 and a handle 104 where, as shown in the cross-sectional view of FIG. 35(b), the handle has two wings 104 (top and bottom). The needle guide also has two spring members 105. In this view, the arrows denoted as C1 and C2 show the direction of displacement for the needle release where C1 are the direction for the handles 104 and C2 are the directions for the needle guide 98. The needle release may be affected by a force against the needle to deform or displace portions of the needle guide.

Tenth Embodiment

The engagement members and needle holders of this embodiment include a means to removably lock the needle into the holder. In these figures, a spring is used to lock the needle in the needle guide 98. As shown in FIG. 36(a), the needle holder includes a needle guide 98 and a support member 102 that is connected to an attachment portion 103 where the attachment portion 103 attaches to the needle positioning apparatus. The support member 102 is connected to a spring member 105 that is further connected to a handle 104. A second spring member 105 connects the handle 104 to a shutter 106. When engaged, the snap hooks 107a and 107b snap together and lock the shutter 106 in place.

The detailed workflow of puncture treatment for a target, such as a tumor, in which an MRI unit is used as a visualization unit, is similar to that in the first embodiment, and descriptions thereof are thus omitted. In the present embodiment, similar to the first embodiment, when multiple-needle puncture is performed, steps similar to those illustrated in FIG. 5 are performed. A method for releasing the needle holders after the needle is inserted will now be described.

First, as illustrated in FIG. 36(a), the spring members 105 are compressed by pushing on the handle 104a, the handle arm moves in the direction E1 and the shutter 106 covers the open side of the through-hole 108 of the needle guide 98 (see FIG. 37(a)). Compression of handle 104b from the locked position in the direction F1 releases snap hooks 107a and 107b and allows displacement in the direction noted as F2 which opens the shutter 106 (see FIG. 37(b)). With the shutter 106 open, a needle can be easily removed from the needle guide 98. FIG. 36(b) is a cross-sectional view of the needle holder of FIG. 36(a) along the axis D-D. Thus, in the present embodiment, the needle can be placed in an engaged position by pressing on handle 104a until snap hooks 107a and 107b engage with each other to lock the needle in the needle guide 98. Engagement of the needle holder can be seen in FIG. 37(a). When the needle is to be released, the handle 104b is presses to disengage the snap hooks 107a and 107b and the needle holder 98 moves to the position shown in FIG. 37(b). The shutter 106 then moves away from the through hole 108 and allows a needle positioned in the through-hole 108 to move out of the needle guide 98 and thus separate from the needle holder.

Thus, as shown in reference to FIGS. 36 and 37, springs may be used to close and/or lock the needle into place by moving a shutter 106 between an open and a locking position. In other embodiments, the needle holder can provide a locking position without a spring—having at least two mode including needle holding and not needle holding. As described herein, springs can be used, for example, to eject the needle(s) from the holder. Where applicable, the different embodiments (e.g., a spring holder and a spring ejector) may be combined into further embodiments.

Eleventh Embodiment-Fiducial Markers

The present application further contemplates the addition of one or more MRI-visible markers as part of the apparatus. This provides, for example, confirmation that the needle is correctly positioned prior to insertion.

MRI-visible fiducial markers which are arranged at predetermined locations on, for example, the base body, and first rotary guide, the second rotary guide, and/or the needle holder. During an MRI-guided intervention, images of these markers are acquired by MRI-scanner to obtain the spatial position and posture of each of these parts. The fiducial markers can serve as a reference, so that needle position and orientation can be tracked with fiducial markers.

Volumetric MRI scans can confirm the position and orientation of the needle's tip, based on fixed reference fiducials (e.g., disposed on the RF-coil attachments) and movable fiducials disposed on at least one of the rotary guides. It is envisioned, for example, an arrangement where, for every needle incision, the position of the manipulator and patient can be registered with respect to the coordinates of the MRI system. During a needle incision procedure, the position of the tip of the needle is also registered with respect to the manipulator, the patient and the MRI system. In apparatus having multiple needle guides, each of the needle guides may have an MRI-visible marker affixed to the needle holder. In some embodiments, the MRI-visible marker will comprise a thin elongated bar or tube that is affixed to the needle guide or other part of the needle holder with the long axis parallel to the needle.

Thus, in some embodiments, after an MRI image is obtained with the needle positioned in the device, a virtual needle trajectory may be determined. In use, after an image is obtained, the offset between the position of the MRI-visible marker and the needle itself can be subtracted to obtain the virtual needle trajectory. In some embodiments, the virtual needle trajectory may be displayed with the MRI image to clearly show the doctor the exact needle position.

The use of fiducial markers with the needle positioning apparatus can be accomplished with a workflow similar to that described in FIG. 5. In some embodiments, fiducial markers are located on at least one of the base, the first rotating member, and the second rotating member such that a single scan can be used for both registering the device and planning needle insertion location. Thus, the fiducials can be used to decrease the number of necessary scans.

The MRI-visible marker contains an MRI imaging medium (or, MRI imaging contrast medium) may be any of number of different types of MRI imaging mediums that are currently known, or that later become known, for purposes of providing an MRI image that visibly contrasts with the surrounding portions of the image. The MRI imaging medium preferably has a medium or high intensity signal. Examples of the MRI imaging mediums include, but are not limited to, ferromagnetic or super-paramagnetic materials such as nickel, iron, cobalt, magnesium, gadolinium, dysprosium, terbium and alloys and oxides thereof as well as iron oxide-based colloids such as ferumoxide and ferumoxsil). Additional MRI imaging mediums include lipids such as those disclosed in U.S. Pat. No. 5,427,099, fluorine 19 (F119) compounds (see U.S. Pat. No. 6,975,896). One or more different MRI imaging mediums may be used. The MRI imaging medium may be used, for example, as a solid material, or mixed with a liquid, gel, or sol.

When applied to other modalities, the fiducial markers need not be readable by MRI-scanners as disclosed above. Instead, the fiduciary markers can be modified to conform to the specific imaging modality (e.g., CT), or can be removed.

Twelfth Embodiment

A twelfth embodiment will now be described with reference to FIGS. 38 to 40. Components similar to those of the above-described embodiments are denoted by the same reference numerals, and descriptions thereof are thus omitted. Engagement members and needle holder will now be described in detail with reference to the drawings. These engagement members and needle holders may be used with the needle positioning units as described herein or other needle positioning units. The design described in this embodiment contemplates a circular needle positioning unit with a circular through-hole for, for example, access to the skin and needle at insertion. However, other similar designs are also within the scope of this embodiment.

In use, where small detachable needle holders are used, once the needle holder is released or removed from the positioning apparatus could potentially be dropped through the middle of the needle positioning apparatus. This is particularly relevant when the needle holder has a small size and when multiple needles are contemplated. Thus, to prevent the needle holder from falling through the rotary guide during the treatment when the needle holder is released or detached, embodiments are provided herewith that provide openings on the rings such that the needle holder can be removed completely from the treatment space.

Figure 38A:
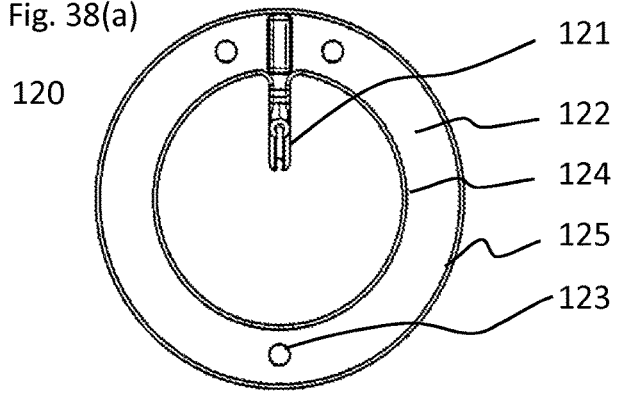
FIG. 38(a) is a top view of a needle positioning apparatus having a ring-shaped engagement member and a needle holder.
Figure 38B:
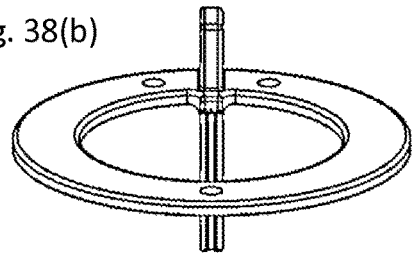
FIGS. 38(b) and 38(c) are perspective views of the apparatus of FIG. 38(a).
Figure 38C:
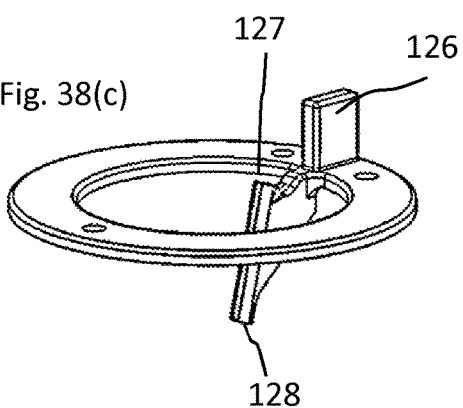
Figure 39A:
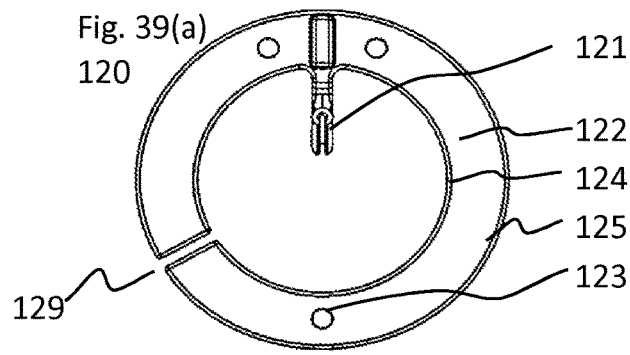
Figure 39B:
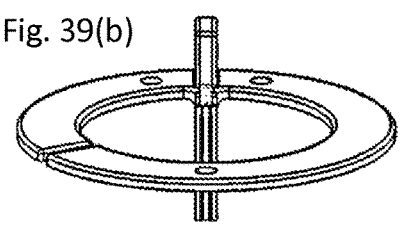
FIGS. 39(b) and 39(c) are perspective views of the apparatus of FIG. 39(a).
Figure 39C:
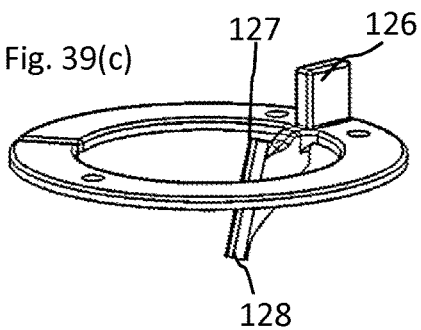
Figure 40A:
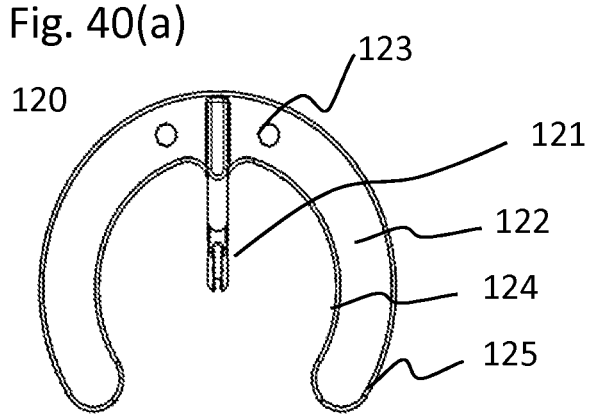
FIG. 40(a) is a top view of a needle positioning apparatus having an open ring-shaped engagement member and a needle holder having a deeper guide.
Figure 40B:
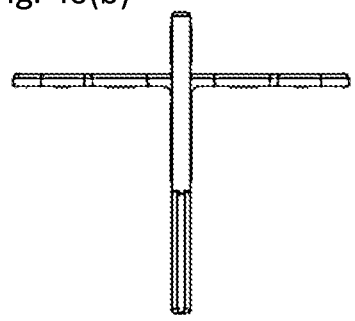
FIGS. 40(b) and 40(c) are perspective views of the apparatus of FIG. 40(a).
Figure 40C:
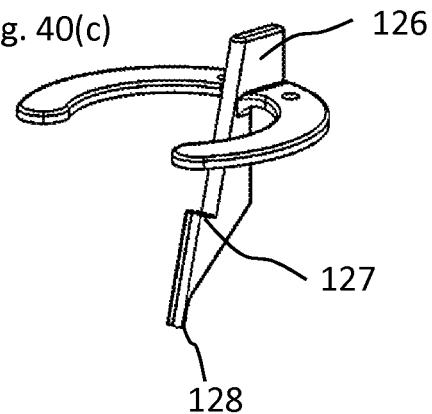

The needle holders 120 as shown in FIGS. 38-40 all have components of the needle holders that are large rings (with our without a slit) or large C-shaped or U-shaped.

These components connect with the second rotating member of the needle positioning apparatus and this prevents the needle holder to fall through the hole in the needle positioning apparatus.

The embodiment shown in FIGS. 38(*a*)-(*c*) is needle holder with an attached portion shaped as a ring. This ring portion of the needle holder 122 attaches to the needle positioning apparatus at the second rotating member (not shown). As discussed above for other embodiments, the needle holder may be sterilized prior to attachment to the needle positioning apparatus. In this embodiment, the inner circle of the ring 124 has substantially the same diameter and sits on the inner circle of the second rotating member (not shown). This embodiment shows the holes on the 123 which are aligned with protruding pins located on the second rotating member such that the needle positioning apparatus and needle holder, when locked with the pins, will be precisely aligned to the appropriate position and will move accordingly. This embodiment shows three holes 123, which would correspond to three pins. However, other embodiments will contain 2, 4, 5, 6, or more holes and pins or may have another means of attachment. The needle holder has a handle 126 so that the user can easily attach or detach the needle holder. While the inner and outer diameters do not need to be identical, in this embodiment, the outer diameter of the ring 125 is larger than the inner diameter of the second rotating member of the needle positioning apparatus such that the needle holder cannot fall into the rotary guide needle guidance mechanism when it is place or when it is removed, such as when it is removed after placing a needle and before placement of another needle or before undergoing, i.e., ablation, or cryotherapy.

The needle guide in FIG. 38 shows C-shaped needle guide. In some similar embodiments, the needle holder 121 may be shaped as any other needle holder shown in the other embodiments as disclosed herein. See for example, FIG. 34. The outer and inner diameters of the ring may be appropriately chosen so as not to fall into the rotary guide.

FIG. 39 provides an embodiment of a needle holder having an open ring shaped attachment. The ring 102 and needle holder features and functions of this embodiment are the same as the embodiment shown in FIG. 38 and are not discussed in detail. In addition to the features described above, this embodiment provides a slit opening 129 on the ring for easy removal of the needle holder after insertion of a needle. Once the needle is inserted into a patient's body, the needle is released from the needle guide and the needle holder is detached from the rotary guide. This can be done by lifting the needle holder off of pins found on the needle positioning apparatus. The needle holder is then moved away from the apparatus such that the inserted needle passes through the slit 129. Thus, the needle holder is removed completely out of the treatment region. As shown in FIG. 39, the slit must be larger than the diameter of the needle and is preferably substantially larger to allow the physician to pass the placed needle through the slit during removal of the needle holder, and is preferably done without contacting the needle and the slit with sufficient force to disturb the patient.

The embodiment shown in FIG. 40 is another open ring embodiment of a needle holder having a partial or C-shaped ring. The needle holder features and functions of this embodiment are similar to the embodiments of FIGS. 38 and 39, with this larger opening for easier removal. This embodiment provides a different placement of the ring shaped attachment 124 to the needle guide 121.

As shown in FIG. 40, the needle guide 121 extends more deeply towards the insertion point than, for example, FIG. 39. The needle holder 121 in this embodiment has its bottom tip 128 further extended closer to the insertion point, which allows the top end 127 of the guide to be closer to the insertion point. With the top end 127 closer to the insertion point, the user is able to insert the needle deeper, creating larger workspace for the treatment with the needle.

Similarly, a feature of the needle holder shown in FIG. 38 is that the needle holder 121 has its bottom tip 128 of the needle holder positioned close to the insertion point respect to the ring. This allows the top end of the guide 127 to be at a height sufficiently closer to the insertion point such that the needle used for therapy is inserted deeper compared to an embodiment with the needle guide positioned higher.

If the needle holder is located some distance away from the insertion point, the needle cannot be used to its full extent and may not be able to extend far enough into a body to reach a target position. Thus, embodiments are provided where the needle holder is lowered relative to the rotary guides to allow for insertion of a longer portion the needle through the insertion point. Thus, by positioning the needle holder closer to the insertion point, the effective length of the needle allows the physician to insert the needle deeper into the patient and have larger workspace, or larger possible treatment area.

Since the patient body may have curvature and extend upwards into the opening of the rotary guide device, in some embodiments, the bottom of the needle holder is to be designed within the height of approximately 20 mm from the bottom plane of the rotary guide device. To limit the uninserted part of the needle to less than 30 mm, the top of the needle holder may be at or lower than 30 mm from the bottom plane of the rotary guide. In other embodiments, it is contemplated that the needle holder is designed such that the bottom of the needle holder has a height of approximately 15 mm, 20 mm or 25 mm from the bottom plane of the rotary guide and the top of the needle holder has a height of less than 20 mm, 25 mm, 30 mm, or 35 mm from the bottom plane of the rotary guide ranging from 10 to 30 mm less than 15 mm.

While, in this embodiment, the needle guides depicted in FIGS. 38-40 contain detachable needle guides, it is contemplated that other needle guides will be combined with the features described as embodiment eleven. For example, the needle guides, or holder members as shown in any one of FIG. 1, 6, 12, 15, 19, 24, 26, or 30 may be used to form the needle holder as described in this embodiment. Thus, instead of, for example, a wedge-shaped, semicylindrical, or cylindrical retaining portion, the needle holder includes a ring-shaped or C-shaped portion to attach the needle holder to the needle positioning attachment.

Similarly, the retaining members as shown in any one of FIG. 1, 6, 12, 15, 19, 24, 26, or 30 which are projecting portions on the needle holders and the sliding portion(s) which are recessed portion(s), are provided on the rotating member. However, in each embodiment, the sliding portions may be provided on the needle holders, and the retaining portions may be provided on the rotating member. It is clear for a person skilled in the art that effects similar to the above-described effects can also be achieved by this modification.

In addition, in the above-described embodiments, a grip-like portion is provided on an end portion of the needle 10 to facilitate the insertion of the needle. This portion can be configured so as to be detachable from the needle. In such a case, the through hole formed by the needle holders serves as an opening for removing the needle holders from the needle that has been inserted into an object by being guided along the through hole, and the needle holders can be removed from the rotating member and the needle by moving the needle holders upward in the longitudinal direction of the needle.

Thirteenth Embodiment

A thirteenth embodiment will now be described with reference to FIGS. 41(a)-41(e). The engagement member and needle holder shown in this embodiment may be combined with the needle positioning unit of the above-described embodiments or other needle positioning units.

Figure 41A:
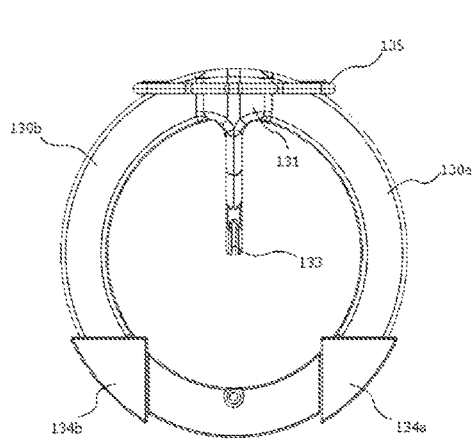
FIG. 41(a) is top view of a needle positioning apparatus having an open ring-shaped engagement member and a needle holder attached to a needle positioning unit.
Figure 41B:
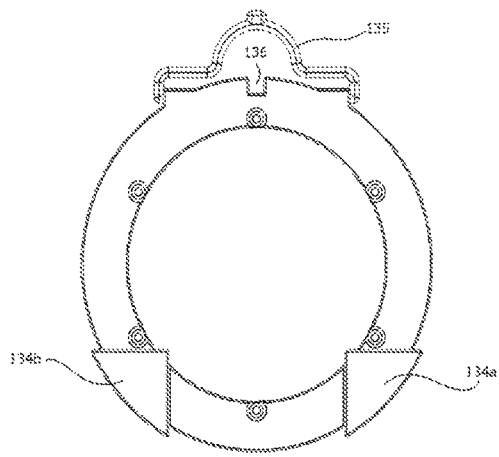
FIG. 41(b) is top view of the mating surface of the needle positioning unit.
Figure 41C:
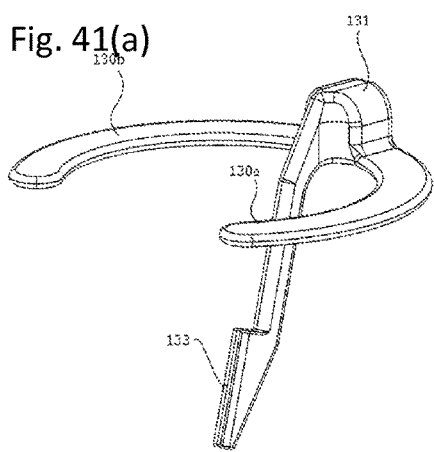
FIGS. 41(c) and 41(d) are perspective views of the engagement member and needle holder of FIG. 41(a).
Figure 41D:
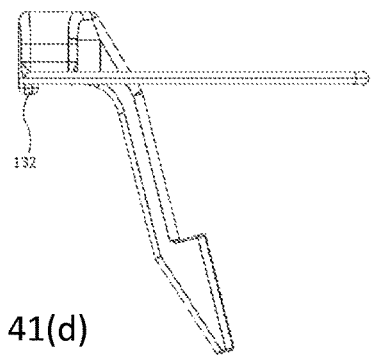
Figure 41E:
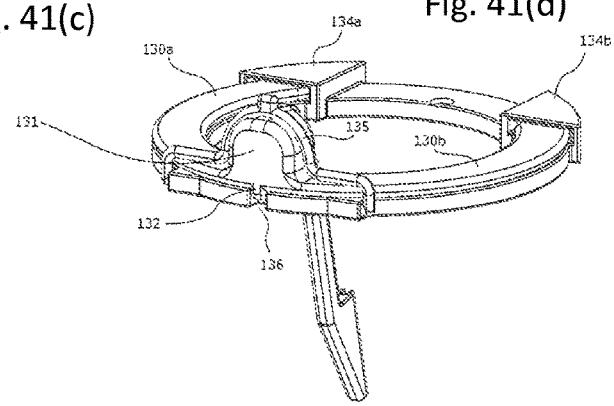
FIG. 41(e) is a perspective view of a needle positioning apparatus of FIG. 41(a).

In FIGS. 41(a) and 41(e), an example of the positioning apparatus where the engagement member securely attaches to the needle positioning unit is shown. For simplicity, only the two mating surfaces are shown, where the remainder of the needle positioning unit is not shown. FIG. 41(a), shows the mating surfaces of the positioning apparatus where the engagement member is secured to the needle positioning unit via insertion of a key 132 on the engagement member into the keyway 136 on the needle positioning unit (not visible in this figure), insertion of the arms 130a-130b of the engagement member into holsters 134a-134b of the needle positioning unit, clasping of the hinge 136 over the handle 131. The separated parts are shown in FIG. 41(b) and FIG. 41(d). FIG. 41(b) shows the mating surface on the needle positioning unit. On this surface are holsters 134a-134b, a hinged clasp 135, and a keyway 136. FIG. 41(c) shows some mating features on the engagement member and needle holder.

Thus, in use, the arms 130a and 130b are slid into the holsters 134a and 134b. The holsters 134a and 134b can cover most of the arms 130a and 130b and prevent the arms 130a and 130b from lifting up away from the top surface of the needle positioning unit. A key located on the engagement member is placed into the keyway 136 and the hinged clasp 135 is rotated to cover the handle 131 (see FIG. 41(d)).

The engagement member and needle holder can be moved onto the top (mating surface) of the needle positioning unit at an angle relative to the top surface of the needle positioning unit. In some embodiments, the engagement member and needle holder are place and/or removed at, for example a 0-80 degree angle relative to the mating surface, or more particularly 30 to 60 degrees. These embodiments allow for less force directed into a patient's body and also avoid placing a needle over any previously placed needle(s).

These features provide a means for fixing the needle holder to the moving part of the needle positioning unit exemplify (a) the use of a protruding portion (e.g., the key 132) that engages a recessed porting (e.g., the keyway 136), (b) the use of an inset porting (the holsters 134a-134b) holding the arms of the engagement member (130a-130b), and (c) the use of a hinging member (e.g., the hinged clasp 135) that holds the hinge receptor (e.g., the handle, 131). One, two, or three of these fixing mechanisms may be used. Other fixing means, or a plurality of the fixing mechanisms as described herein may be used together to fix the needle holder onto the needle positioning unit.

FIG. 41(d) provides another view of the mating feature on the engagement member and needle holder. This feature is the key 132. In use, the key 132 is fitted into a keyway 136. This feature is advantageous since it allows a physician to physically feel when the needle holder is correctly placed on the needle positioning unit when the key drops into the keyway. Also the physician can tangibly detect whether the needle holder is mounted in an incorrect position by feeling that there is an irregular gap between the key and the keyway. There may be 1, 2, 3, 4, or more keys and keyways and they may either be placed as shown with the key on the engagement member or, conversely the key (or keys) may be placed on the needle positioning unit.

In FIG. 41(e), it is shown that the engagement member and needle holder can be placed on to the top surface of the needle positioning unit and the arms 130a-130b can slide into the holsters 134a-134b. These holsters 134a-134b prevent the arms 130a-130b from being lifted away from the top surface of the needle positioning unit. They also prevent the needle holder from rotating about the center of the ring. In this figure, the engagement member is secured to the needle positioning unit via insertion of a key 132 on the engagement member into the keyway 136 on the needle positioning unit, insertion of the arms 130a-130b of the engagement member into holsters 134a-134b of the needle positioning unit, clasping of the hinge 136 over the handle 131.

In FIG. 41(e), the key 132 on the bottom of the engagement member is shown to slide into the keyway 136 on the top surface of the needle positioning unit. The arms 130a-130b will not be able to slide into the holsters 134a-134b unless the key 132 is also properly aligned with the keyway 136.

For added assurance of engagement, the user can determine if the needle holder is properly seated by running their finger along the circumference of the mating surface and feeling if the outside of the key 132 is not flush with the needle positioning unit. This key 132 will prevent the needle holder from moving any direction except radially away from the center of the ring or perpendicularly away from the top surface of the needle positioning unit. The key 132 can be manufactured to have a tight fit to the keyway 136. This will require additional force to place into keyway 136 and to remove from the keyway 136. This extra force can prevent the guide from becoming misaligned accidentally during use.

In FIG. 41(e), the needle holder is shown to be secured to the top surface of the needle positioning unit using a hinged clasp 135. This clasp 135 has a shape that matches the profile of the handle 131 on the needle holder. This feature provides a means to prevent this clasp 135 from latching if there is a misalignment. When the clasp 135 is latched to the handle 131 on needle holder, it is forced into tension by the curved profile on the top of the handle 131. This force keeps the needle holder pressed firmly against the top surface of the needle positioning unit. The positioning of this clasp 135 and handle 131 allows the needle holder to be placed and latched with a single hand. Also, this clasp 135 can optionally provide clicking feel to the physician in the event of mounting as the clasp is locked into place. With this, the physician can confirm whether the needle holder is mounted properly only by using tactile sense. Moreover, the physician pushes or pulls the clasp 135 in a direction parallel to the patient's skin when the physician mounts and/or dismounts the needle holder on the robot that is located on the patient. Therefore, the clasp 135 can avoid pushing the needle holder with the robot into the patient with too large force and improve the patient comfort in the event of attachment and/or detachment of the needle holder on the patient-mount robot.

The apparatus of guiding the needle is described with reference to FIG. 41(c). In FIG. 41(c), the needle holder portion of the needle guide is formed by a slotted channel 133. This channel 133 allows the needle to be quickly inserted and aligned. The user can secure the needle inside the channel 133 while inserting by pressing a finger or other apparatus against the opening in the channel 133 to prevent the needle from deviating from the trajectory.

Thus, the use of the apparatus described in this embodiment provides some particularly advantageous features. For example, the engagement member and needle holder can be seated onto the mating surface of the needle positioning unit by sliding it into place from an angle—first sliding the arms 130a-130b into the holsters 134a-134b, seating the key 132 into the keyway 136 and then latching the hinge 135 onto the handle 131. This can be done with a single hand and with little to no force directed either horizontally or vertically or in the movement direction of the needle. The engagement member and needle holder can be placed either with or without a needle in the needle guide. If no needle is present, the needle can simply be placed into the guide and inserted into the desired position. This embodiment provides for easy and simple release of the engagement member after needle insertion, where a second or additional engagement member and needle guide may then be mated to the needle positioning unit for additional needle placement.

Fourteenth Embodiment

Figure 42A:
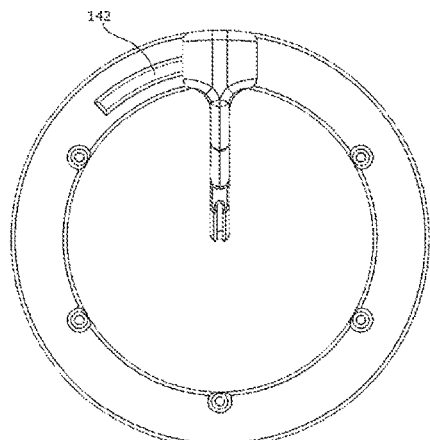
FIG. 42(a) is top view of a needle positioning apparatus having an open ring-shaped engagement member and a needle holder attached to a needle positioning unit.

The fourteenth embodiment of the present invention, an apparatus of attaching the needle holder to the needle positioning unit, will be described with references to FIG. 42(a)-42(f). In FIG. 42(a), an exemplary embodiment example of the attachment is shown. For simplicity, only the two mating surfaces are shown. However, the engagement member and needle holder shown in this embodiment may be combined with the needle positioning unit of the above-described embodiments or other needle positioning units.

Figure 42B:
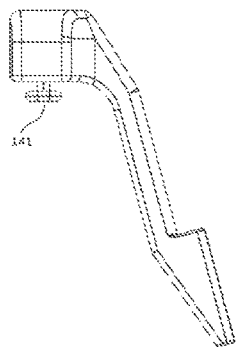
FIGS. 42(b) and 42(c) are perspective views of the needle holder of FIG. 42(a).
Figure 42C:
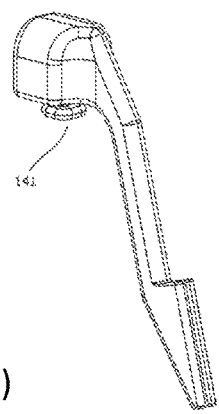
Figure 42D:
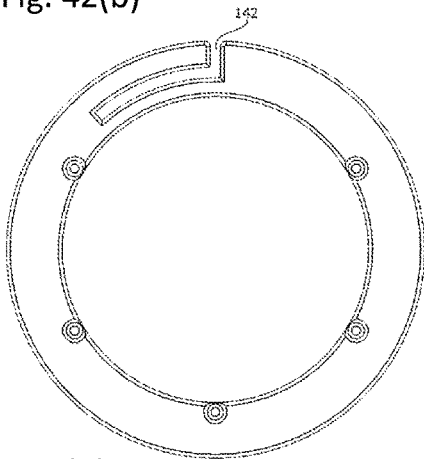
FIG. 42(d) is a top view of the mating surface of the needle positioning unit.
Figure 42E:
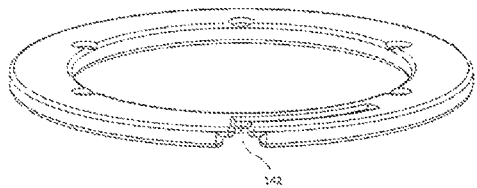
FIG. 42(e) is a perspective view of FIG. 41(a).

In the exemplary embodiment shown in FIG. 42(a), the mating surface of the needle positioning unit has a keyway that allows the needle holder to be inserted and rotated to lock. FIG. 42(b), and FIG. 42(c), show the engagement member and needle guide including a key 141. This key 141 has a non-linear profile. FIG. 42(d), and FIG. 42(e), show the keyway 142 on the needle positioning unit. The profile of this keyway 142 permits the key 141 of the needle holder to be inserted. This profile prevents the needle holder from being lifted perpendicularly away from the top surface of the needle positioning unit.

In FIG. 42(a), the keyway 142 is shown to have a non-linear path. When the needle holder is inserted into the keyway 142, it can follow this path. Other paths are similarly contemplated, and include paths with a curved path instead of sharp turn or an additional turn at the end to latch the key into the keyway. With these key and keyway features, the physician can simply slide the needle holder to the parallel direction to the patient's skin when the physician mounts and/or dismounts the needle holder on the robot that is located on the patient. Therefore, this embodiment can also avoid pushing the needle holder with the robot into the patient with too large force and improve the patient comfort in the event of attachment and/or detachment of the needle holder on the patient-mount robot.

Figure 42F:
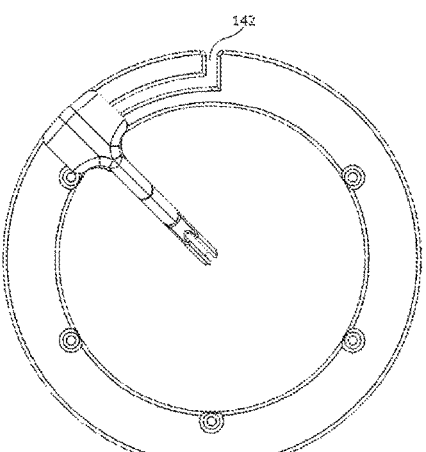
FIG. 42(f) is top view of a needle positioning apparatus having an open ring-shaped engagement member and a needle holder attached to a needle positioning unit.

In FIG. 42(f), the needle holder is shown when positioned at the end of the keyway 142. The shape of the key 141 prevents the needle holder from rotating or from moving radially away from the center of the ring. As above, additional engagement means, such as sliding arms and holder and a latching hinge may also be included as part of this embodiment.

Fifteenth Embodiment

Figure 43A:
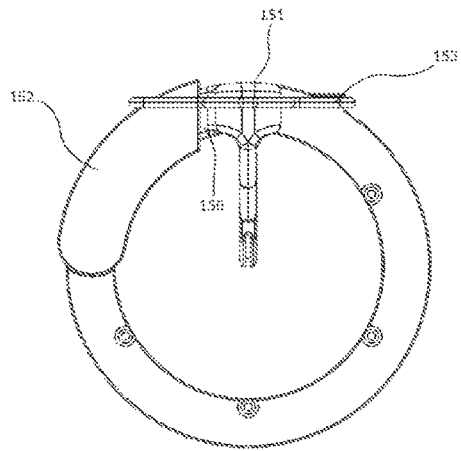
FIG. 43(a) is top view of a needle positioning apparatus having an open ring-shaped engagement member and a needle holder attached to a needle positioning unit.

The fifteenth embedment of the present invention, an apparatus of attaching the engagement member and needle holder to the needle positioning unit, will be described with reference to FIGS. 43(a)-43(e). In FIG. 43(a), an example of the apparatus with the configuration as described in this embodiment is provided. For simplicity, only the two mating surfaces are shown. The apparatus shown in FIG. 43(a) is similar to the apparatus of the thirteenth embodiment except that only a single arm is provided on the engagement member.

Figure 43B:
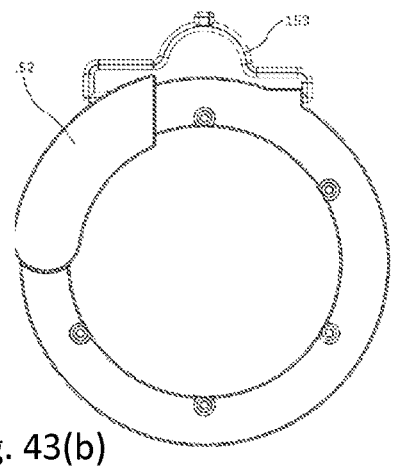
FIG. 43(b) is a top view of the mating surface of the needle positioning unit.
Figure 43C:
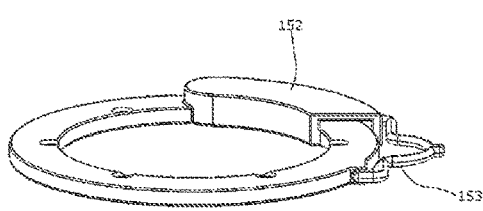
FIG. 43(c) is a perspective view of the mating surface of FIG. 43(b).
Figure 43D:
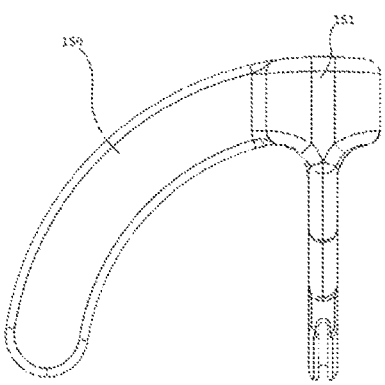
FIG. 43(d) is a perspective view of the engagement member and needle holder of FIG. 43(a).
Figure 43E:
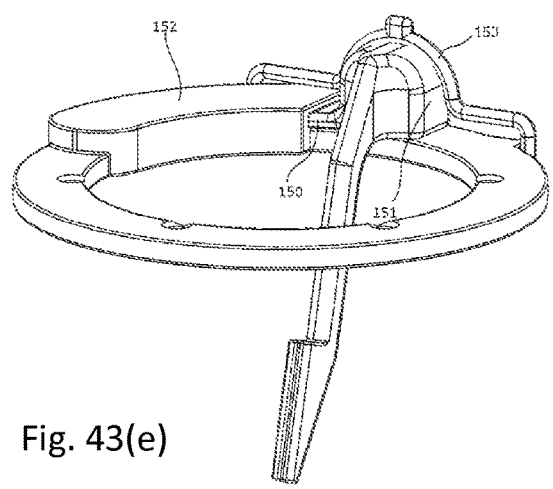
FIG. 43(e) is perspective view of the apparatus of FIG. 43(a).

FIG. 43(b) and FIG. 43(c) show the mating surface on the needle positioning unit. On this surface, there is a holster 152 and a hinged clasp 153. FIG. 43(d) shows some mating features on the engagement member and needle holder. These features are an arm 150 and the handle 151. In FIG. 43(e), the engagement member and needle holder are shown placed on the top surface of the needle positioning unit. It can be rotated about the center of the ring to insert the arm 150 into the holster 152. This holster 152 can cover most of the arm 150 and prevent the arm 150 from lifting up away from the top surface of the needle positioning unit.

In FIG. 43(e), the needle holder can be secured to the top surface of the needle positioning unit using a hinged clasp 153. This clasp 153 has a shape that matches the profile of the handle 151 on the engagement member. This feature will prevent this clasp 153 from latching if there is a misalignment. When the clasp 153 is latched to the handle 151, it is forced into tension by the curved profile on the top of the handle 151. This force keeps the needle guide pressed firmly against the top surface of the needle positioning unit.

In yet other embodiments, the apparatus as shown in FIG. 43 is provided with one or more keys and keyway. In other embodiments, there are one or two arms on the engagement member that may be of differing lengths. Similarly, the holster 152 may be shorter or longer as appropriate for differing devices. The holster provides a means to secure the arm onto the needle positioning unit and prevent movement either rotationally or to prevent the engagement member from lifting away from the mating surface.

The length of the arms in FIGS. 40, 41, and 43 are not meant to be limiting. In some embodiments, the arms may be significantly shorter or longer than the arms depicted in these embodiments.

Sixteenth Embodiment

A sixteenth embodiment will now be described with reference to FIGS. 44 and 45. Components similar to those of the above-described embodiments are denoted by the same reference numerals, and descriptions thereof are thus omitted.

FIG. 44(a), FIG. 44(b), and FIG. 44(c) show a needle positioning apparatus 201 where the needle is in the needle holders 208 and 209 (FIG. 44(a)), and where the needle holders 208 and 209 are open (FIG. 44(b) and where the needle holders 208 and 209 are removed from the needle positioning apparatus 201. FIG. 45 is a schematic perspective view of needle holders 208 (FIGS. 45(a)) and 209 (FIG. 45(b)).

The needle holders 208 and 209, which hold the needle 10, will be described in detail with reference to the drawings. Similar to the above-described embodiments, the needle holders 208 and 209 form a through hole when semi-cylindrical grooves 208a and 209a are in contact with each other, the through hole being capable of holding the needle in a 360-degree rotatable manner and guiding the needle in the longitudinal direction thereof. Needle holder members 208 and 209 as needle holding units are provided on the second rotating member 25. The needle holder members 208 and 209 respectively include cylindrical retaining portions 208b and 209b and divided portions 208c and 209c. Also, two sliding portions 55b are formed in a top surface of the second rotating member. The needle holder 208 is rotatable around a central axis of the retaining portion 208b which is cylindrical when the retaining portion 208b is engaged with the sliding portion 55b provided on the second rotating member. So does the needle holder 209.

As described in FIGS. 45(a)-(b), the needle holders 208 and 209 include gear wheels 208d and 209d which have the identical rotating axis of the retaining portion 208b and 209b, and as shown, the gear wheel 208d engages with the gear wheel 209d. An actuator 210 also comprises a gear wheel (not shown) and the gear rotates around a rotation axis when the actuator 210 is being operated. The gear wheel of the actuator 210 (not shown) engages with the gear wheel 209d, the actuator is configures to have the gear wheel 209d rotate around the rotation axis of the retaining portion 209b. The gear wheel 208d rotates around a rotation axis of the retaining portion 208b and in the inverse rotating direction of the gear wheel 209d according to the rotation of the gear wheel 209d. The gear wheel 208d rotates by the same rotation displacement or the same rotation angle as the gear wheel 209d rotates.

In the present embodiment, after a physician punctured the needle 10 described in FIG. 44(a) into a patient's body, the physician turns on a switch to drive the actuator 210 and needle holders 208 and 209 are opened by the actuator 210 so the needle holders are separated from the needle 10 (FIG. 44(b)). After that, the physician removes the needle holders 208 and 209 from the needle positioning apparatus (FIG. 44(c)). Thus, the physician can remove the needle holder from the positioning apparatus more safely since the needle holders 208 and 209 are separated by the actuator and the needle 10 is released.

In the present embodiment, the needle holder and the gear wheel can both be made as a disposable component. For example, the needle holder and the gear wheel can be manufactured integrally by resin-forming method at a low cost. Thus, these components can be single use components that do not have the inherent difficulty of requiring a sterilization step after use, simplifying workflow and reducing the potential risk of infection.

In the present embodiment, the opening/closing structures including the two gear wheel 208d and 209d and actuator 210. However, the present invention is not limited to this embodiment. The needle positioning apparatus 201 may include two actuators. The respective actuators are assigned to respective the gear wheel 208d and 209d for rotating the respective needle holders 208 and 209. Also, the both needle holders and actuator(s) may be removable from the needle positioning apparatus 201. Also, the other transfer means such as traction rollers that are driven by the friction may be used instead of the gear wheels 208d, 209d and the gear wheel of the actuator 210. In addition, variety of a transfer means for transmission of force and torque such as a belt, pulley, wire and so on can be applied to the needle holders 208 and 209 and the actuator 210. In some embodiments, the actuators are located on the moving portion of the needle positioning unit, or they actuators may be located on the engagement member or alternatively on the needle holder.

Seventeenth Embodiment

Figure 48:
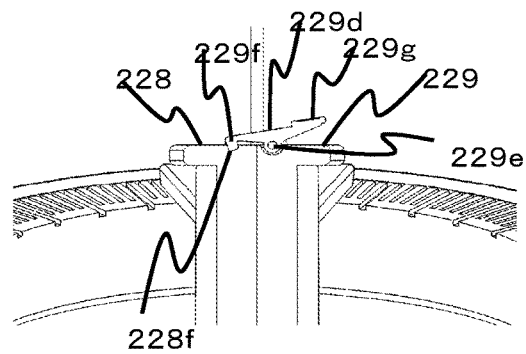
FIG. 48 is a schematic sectional view of the needle folders 221 illustrated in FIG. 44.
Figure 49A:
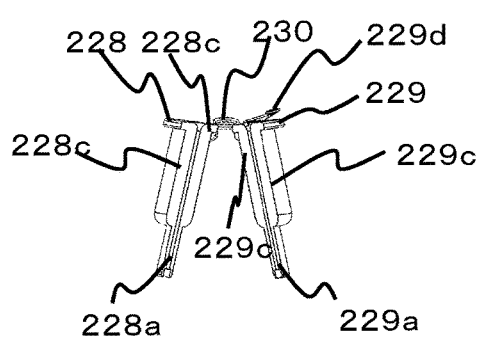
FIG. 49(a) and FIG. 49(b) are schematic perspective views of needle holders 228 and 229.
Figure 49B:
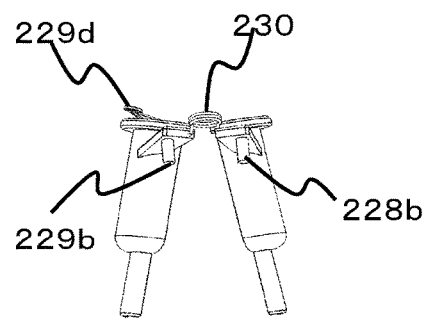

A seventeenth embodiment will now be described with reference to FIGS. 46 to 49. Components similar to those of the above-described embodiments are denoted by the same reference numerals, and descriptions thereof are thus omitted. FIGS. 46(a)-(b) and 47(a)-(b) provide a needle positioning apparatus 221 and FIG. 48 is a schematic sectional view of the needle positioning apparatus. FIG. 49(a)-(b) provide views of the needle holders 228 and 229.

Similar to the above-described embodiments, the needle holders 228 and 229 form a through hole when semi-cylindrical grooves 228a and 229a are in contact with each other, the through hole being capable of holding the needle in a 360-degree rotatable manner and guiding the needle in the longitudinal direction thereof. The needle holders 228 and 229 as needle holding units are provided on the second rotating member 25. The needle holders 228 and 229 respectively include cylindrical retaining portions 228b and 229b and divided portions 228c and 229c. Also, two sliding portions 55b are formed in a top surface of the second rotating member. The needle holder 228 is rotatable around a central axis of the retaining portion 228b which is cylindrical when the retaining portion 228b is engaged with the sliding portion 55b provided on the second rotating member. The needle holder 229 is similarly formed.

As described in FIG. 49, the needle holders 228 and 229 are connected to each other by a compression-torsion spring 230. The divided portions 228c and 229c are separated each other and needle holders 228 and 229 open when the compression-torsion spring is being released from the needle holders 228 and 229.

Next, a stopper 229d that is attached to the needle holder 229 will be described in detail. FIG. 48 is a schematic sectional view of the needle positioning apparatus 221, the sectional view including a longitudinal direction line on the stopper 229d. The stopper 229d can rotate around a rotation axis 229e that is provided as a part of the needle holder 229. Also, a convexity portion 229f is provided at a distal end of the stopper 229d and a concavity portion 228f is provided on the needle holder 228. The condition where the needle holder is in a closed state described in FIGS. 46(a) and 47(a) are formed when the convexity portion 229f engages with the concavity portion 228f and the compression-torsion spring 230 is being compressed because of receiving counterforce from the needle holders 228 and 229.

Figures 46A, 46B:
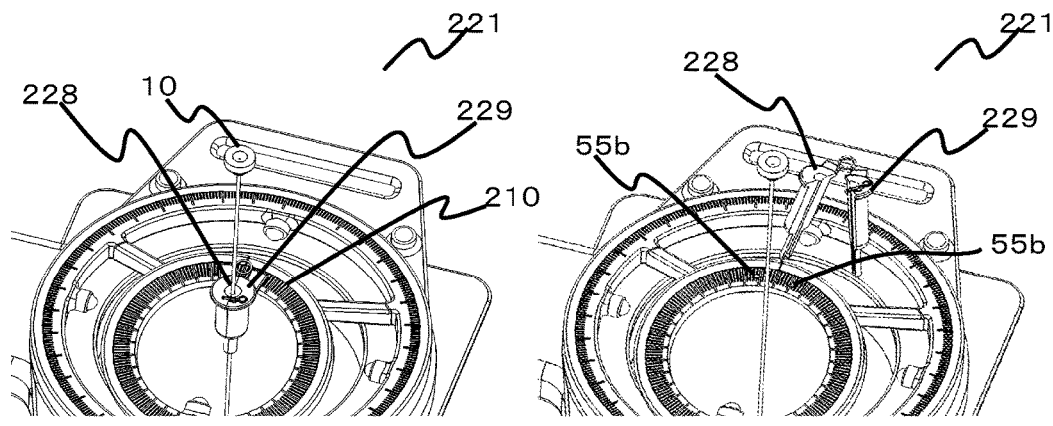
FIG. 46(a) and FIG. 46(b) are schematic perspective views of a needle positioning apparatus 221.
Figures 47A, 47B:
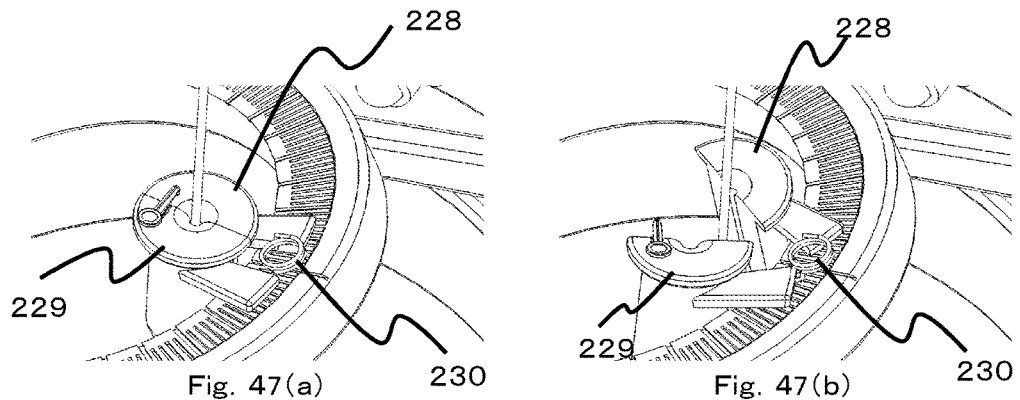
FIG. 47(a) and FIG. 47(b) are other schematic perspective views of a needle positioning apparatus 221 illustrated in FIG. 46.

In the present invention, after a physician punctured the needle 10 described in FIGS. 46(a) and 47(a) into a patient's body, the engagement of the convexity portion 229f and a concavity portion 228f is released by restoring force of the compression-torsion spring 230 when the physician pushes/ presses a pressing section 229g in a vertical direction. Then, as illustrated in FIG. 47(*b*), the needle holders are kept in an opened state. After that, the physician removes the needle folders from the needle positioning apparatus (FIG. 46(*b*)).

According to the present embodiment, the physician can remove the holders from the positioning apparatus more safely because the physician can remove the needle under the condition where the needle 10 and needle holders 228 and 229 are being separated.

In the present embodiment, because the pressing portion 229g, provided near the needle 10, is pressed in a parallel to longitudinal direction of the needle 10, the effect that reduces the external force that is applied to a side surface of the needle 10 via the through hole formed by the semi-cylindrical grooves 208*a* and 209*a* when the physician removes the needle holders from the needle positioning apparatus 221. In other words, it's possible to minimize bending moment of the needle 10 that is applied to the needle 10 and with a punctured portion as the fulcrum when the physician removes the needle holders from the needle positioning apparatus 221.

In the present embodiment, the needle holders and the compression-torsion spring 230 can be made as a disposable component. In some examples, the needle holders and the compression-torsion spring 230 are manufactured integrally by resin-forming method and can be provided at a low cost.

In the present embodiment, the spring can be formed from resin or similar materials because the influence of the creep deterioration of the spring can be considered as small and the time the energizing by the needle holders 228 and 229 are applied to the spring is only when punctual operations are performed.

In addition, because the needle holders can be opened with the simple mechanical structure, the weight of the rotation member becomes lighter. In addition, even if the needle holders are used every time, a sterilization step performed after using them can be omitted. This can simplify an operation workflow and the total cost of the operation can be reduced.

In the present invention, the compression-torsion spring 230 as an energizing means is explained above but the present invention is not limited to this embodiment. The spring for opening the needle holders may be integrated with the needle holders or may be provided separately from the needle holders. Also, the present embodiment is not limited to a compression spring and a torsion spring. A straight-motional spring or a tension spring may be used instead of the compression-torsion spring 230 as an energizing means. Also, a variety of fixing means such as a snap-fit mechanism, a tape, Velcro tape or a magnet may be used instead of an engagement means of the convexity portion 229*f* and a concavity portion 228*f*.

Eighteenth Embodiment

Figure 51:
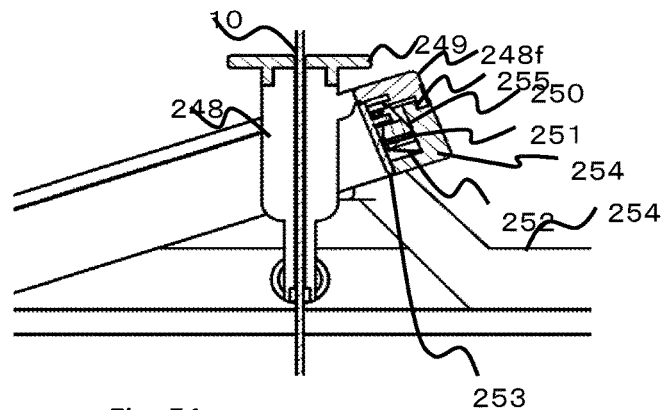
FIG. 51 is a schematic sectional view of the needle positioning apparatus 241.
Figure 52A:
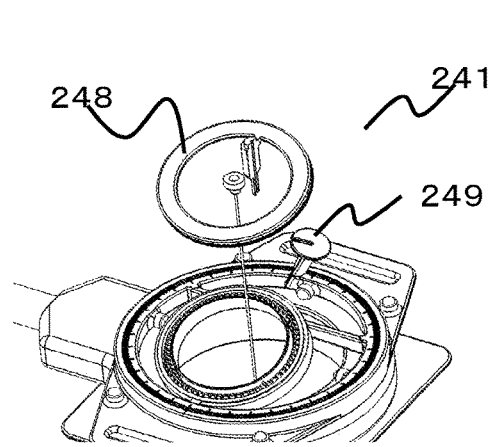
FIG. 52(a) and FIG. 52(b) are additional schematic perspective views of a needle positioning apparatus 241.
Figure 52B:
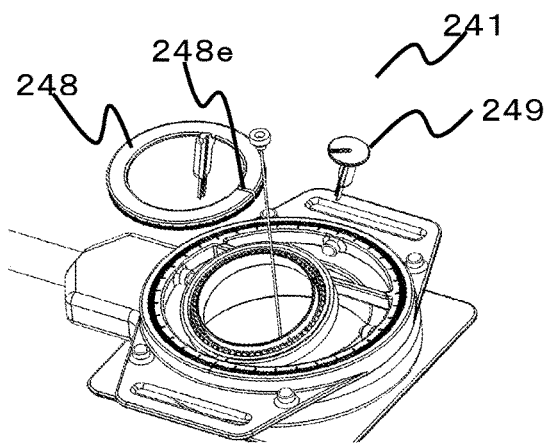
Figure 53A:
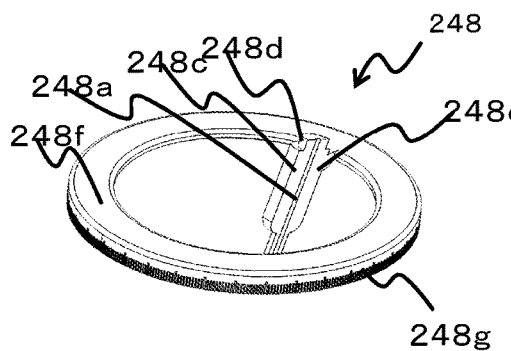
FIG. 53(a) and FIG. 53(b) are schematic perspective views of engagement member 248 and needle holder 249.
Figure 53B:
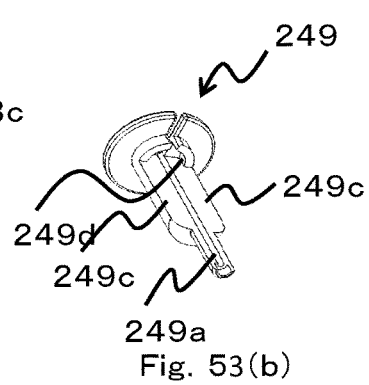

An eighteenth embodiment will now be described with the reference to FIG. 2 and FIG. 50 to FIG. 53. Components similar to those of the above-described embodiments are denoted by the same reference numerals, and descriptions thereof are thus omitted. FIGS. 50 and 52 are a schematic perspective views of a needle positioning apparatus 241 and FIG. 51 is a schematic sectional view of the needle positioning apparatus 241 and FIG. 53 is a schematic perspective views of the engagement member 248 and needle holders 249. Note, FIG. 51 is a schematic sectional view of the needle positioning apparatus when the needle positioning apparatus is cut at the same section as FIG. 2. Hatched lines are applied to the cutting section.

In the preset embodiment, the RCM mechanism of the needle positioning apparatus is common to the mechanism in FIG. 2. In the present embodiment, an ultrasonic motor is exemplified as a positioning device of a rotation angle around the axis 12. First, structures of ultrasonic motor that is embedded to the needle positioning apparatus will now be described with the reference numbers.

In FIG. 51, 250 is elastic member. An electromechanical energy conversion element 251 is attached to the elastic member 250 by a bonding agent or adhesive agent (not shown) and the elastic element and the electromechanical energy conversion element 251 are integrally formed and operates as a vibrator. An electrical circuit such as a flexible board is bonded to the electromechanical energy conversion element 251 and the vibrator generates traveling wave/ progressive wave by applying different-phase AC voltages to the electrical circuit. A rotor 248*f* that is part of an engagement member 248 presses the elastic member 250 with a predetermined pressure that is realized by the disc spring 252. The vibrator, the electrical circuit and the disc spring 252 are supported by the first rotating member and casing 253 and the first rotating member and the casing 253 are mechanically connected each other. Also, the rotor 248*f* is rotatable and rotates with respect to the first rotating member 254 and around the rotation axis 12 via a sliding bearing 255.

Next, the material of each portion of an ultrasonic motor will now be described. As the materials of the elastic element 250, partially stabilized zirconia, silicon nitride, and fine ceramic such as alumina can be used in addition to general metal materials. For rotor 248*f*, the material selection for acquiring stable sliding characteristic and antiwear characteristic is preferable. The rotor 248*f* can be formed with the material hardened by applying, for example, alumite treatment or nitriding treatment onto a surface of magnesium-based aluminum alloys, a fiber reinforced engineer plastic such as PEEK-CF30 and so on, a fine ceramic such as partially stabilized zirconia or aluminum oxide.

In addition, in order to improve the friction condition between the elastic member and rotor 248*f*, a friction member (not shown) may be provided on a sliding surface of the elastic member and/or the moving member. Also, it's possible to make both a part that holds the needle 10 and a sliding friction part integrally by molding injection and to use the different materials to each part. Also, the both parts may be made separately and the made parts may be adjoined to integrate them.

The electromechanical energy conversion element 251 may be formed by piezo electric ceramic such as lead zirconate titanate ($PbZrO_3$—$PbTiO_3$). The disc spring may be made from, in addition to general steel materials for a spring, (i) a high toughness ceramic such as a partially stabilized zirconia or silicon nitride, (ii) an engineering plastic such as a polycarbonate (PC) or Polyether ether ketone (PEEK) or (iii) a cheaper general plastic.

The needle holders 248 and 249, which hold the needle 10, will be described in detail with reference to the drawings. Similar to the above-described embodiments, the needle holders 248 and 249 form a through hole when semi-cylindrical grooves 248*a* and 249*a* are in contact with each other, the through hole being capable of holding the needle in a 360-degree rotatable manner and guiding the needle in the longitudinal direction thereof. In the present embodiment, a rotor 248*f* corresponding to the second rotation member described above-embodiments and an engagement member 248 are made integrally.

The engagement member 248 and needle holder 249 have fitting portions (projection portions) 248d and 249d and divided portions 248c and 249c. The detailed explanation of the fitting portion and the divided portion will now be omitted because the function of the fitting portion and the divided portion are common to the functions of needle holder of FIG. 22 in the fifth embodiment. Also, the engagement member may have a scale portion 248g on a side. The scale portion 248g has the same function as scale portion 4a described above.

Figures 50A, 50B:
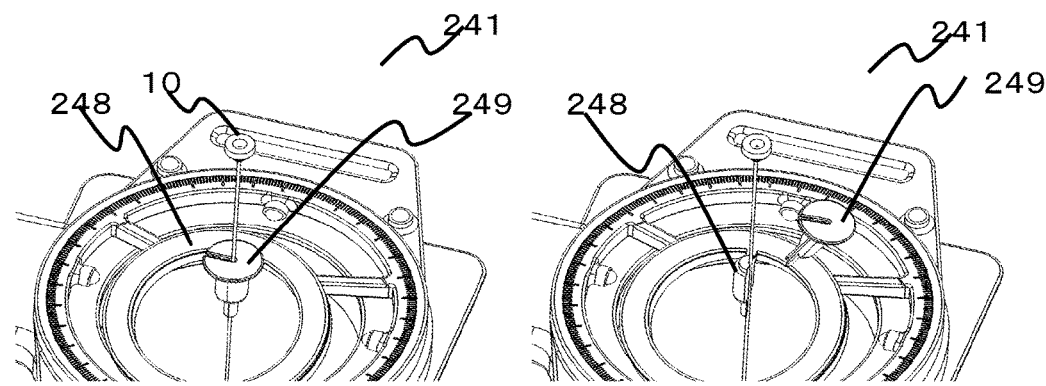
FIG. 50(a) and FIG. 50(b) are schematic perspective views of a needle positioning apparatus 241.

In the present invention, after a physician punctured the needle 10 described in FIG. 47(a) in to a patient's body, the physician removes the needle holders from the needle positioning apparatus (FIG. 50(a)). After that, the physician removes the engagement member 248 by pulling it away from the positioning apparatus along the axis 10 of the needle as described in FIG. 51(a). When a wire or articulated link structure is connected to the needle 10 and the wire or the articulated link structure extends through a ring of the engagement member 248, it may be difficult to remove the engagement member 248 having a close loop shape. To resolve this issue, the engagement member 248 in this embodiment has a notched part 248e for removing the engagement member 248 away from the needle positioning apparatus as described in FIG. 52(b). The size of the notched part 248e is bigger than the diameter of the needle 10, the wire or the articulated link structure. In other embodiments, the engagement member may be shaped with a larger gap such as provided in embodiments thirteen and fifteen.

In the present embodiment, the needle holder that has the rotor for the ultrasonic motor can be made as a disposable component easily. Because the needle holder can be manufactured integrally by resin-forming method at a low cost. Especially, the disposable needle holder realizes to reduce the risk of lowering a reliability caused by the change of friction characteristics of rotor 248f when the elastic member is made from the hard material. In addition, it realizes to omit a sterilization step and the physician can expect a reduction of cost for an operation by treating the exposed rotor as a disposable component.

In the present embodiment, the physician can remove the rotor 248f after the physician punctured the needle 10 into a patient's body; thus, there is only a short period of time that the disc spring 252 is compressed. In this situation, the engineer plastic or the cheap general plastic can be used as material for a pressure member, such as a disc spring, of an ultrasonic motor because it's not required a creep resistance for a long time. This material selection contributes to cost reduction and lightweight.

In the present embodiment, although the structure in that the needle holder and the rotor that is part of an ultrasonic motor are made integrally above, the present invention is not limited to this embodiment. For instance, although the structure of holder having the open loop shape by providing a notched part 248e is explained above, it's assumed that the engagement member 248 of this embodiment comprise two parts that are dividable when the physician remove the engagement member 248. In the present embodiment, although the engagement member 248 that has a scale portion 248g and uses it for measuring a position is explained above, it's assumed that an electrical device for detecting a position such as an encoder instead of the scale portion.

In the present embodiment, although the example to use the ultrasonic motor for rotational driving around the rotation axis 12, it's assumed to use another type actuator other than an ultrasonic motor. Also, an ultrasonic motor or other type actuator may be used for rotation driving around a rotation axis 11. In addition, although the example to use a ring shape motor with a ring shape elastic member, the present invention is not limited to this. It's assumed to drive the needle positioning apparatus by using a linear motion type ultrasonic motor, gear, belt and so on. In the present embodiment, although the example to use the disc spring 252 as the pressure member of the ultrasonic motor, variety of springs, such as a wave washer, a coil spring and a plate spring may be applied instead of a disc spring.

Thus, this embodiment as well as the previously disclosed embodiments provide a means of releasing the needle from the needle holder without, for example, manual compression to dislodge a needle from the needle holder since such an action may be difficult giving the physical constraints of the needles as placed, the risk external force being applied to the patient by the removal, and any complications from the doctor manipulating small devices. Thus, these embodiments provide a needle releasing mechanism adapted to release the needle via an energizing mechanism such as an actuator, spring, or electromechanical energy conversion element. However, other types of springs and energizing mechanisms may alternatively be used.

Additional Embodiments

In some of the embodiments as described herein above, the apparatus may contain one or more lights, such as white LED lights, to provide illumination of the area of the patient's skin and allow better visualization for needle insertion. For example, LED lights may be placed on the inside of the base or the first rotating member and directed into the central hole such that, when placed on the patient, the incision site and surrounding skin will be illuminated. In some embodiments, two, three, four, five, or more lights are located on the device to provide such illumination.

The apparatus may also comprise a translational stage attached to the base of the apparatus. The addition of a translational stage allows for controlled movement, in either one or two directions, to facilitate multiple needle placements. For example, in one workflow, after the needle placement trajectory is planned and a first needle (or first several needles) is inserted into the insertion site, the first needle is released from the needle holder and then the needle holder may be removed from the needle placement apparatus. The apparatus is then translated in one direction and then another needle is inserted. This is particularly useful when the insertion site is large or a greater number of needles are required. In some embodiments, in addition to or instead of the x-y translational stage, a moveable stage allowing controlled movement towards and away from the patient may be provided. In some embodiments, the translational stage allows for only a single axis of movement.

Thus, several embodiments of the needle positioning apparatus as provided herein allow for a workflow where one or more needles are placed in a patient and released from the needle positioning unit. The needles can also be released from the needle holder. Thus, this embodiment provides a large area inside the needle positioning unit where the inserted needles are free to move (e.g., due to breathing of the patient) and also are provided with the needle holder removed to allow, for example, a physician to feel and optionally manipulate the patients skin. If desired, a confirmatory MRI or other image may be obtain with the inserted needles in the patient and with the needle positioning unit still in place, surrounding the insertion site but not used to hold the needle(s) post insertion. Thus, this process provides particular advantage in that no additional piece or support is needed to support the needles when taking the confirmatory image, the physician has access to the area of the skin around the insertion site, and, if required, additional needle(s) may be placed based on information gained from the confirmatory image with needing to re-register the device since the device of some of these embodiments may be placed inside the imaging modality.

In some embodiments, there is provided a positioning apparatus comprising: a needle holder having a through hole that is adapted to at least partially surround a needle to guide the needle in a longitudinal direction; and a needle positioning unit having at least two degrees of freedom, which holds the needle holder and moves together with the needle holder so as to position the needle holder, wherein the needle positioning unit includes an engagement member that fixes a position of the needle holder with respect to the needle positioning unit, the needle holder at least partially detachably attached to the engagement member.

In some embodiments, the needle holder comprises a first needle holder part and a second needle holder part, the first needle holder part and the second needle holder part together forming the through hole, and wherein the needle holder does not guide the needle when the first needle holder part and the second needle holder part are at least partially separated. In some more particular embodiments, the first needle holder part and the second needle holder part are coupled along an axis such that at least one of the first needle holder part and the second needle holder part is adapted for rotation about the axis, and wherein rotation of one or both of the first needle holder part and second needle holder part results in the release of a needle within the needle holder. In some more particular embodiments, at least one of the first needle holder part and the second needle holder part is connected to a fixing member of the needle holder via a rotating member, the fixing member of the needle holder being engageable with the engagement member, and wherein the at least one of the first needle holder part and the second needle holder part that is connected to the fixing member of the needle holder via the rotating member rotates about the rotating member.

In some embodiments, the needle positioning unit comprises the two ring apparatus having two slanted rotary guides as described in U.S. Pat. Pub 2014/0275979 and which is herein incorporated by reference. Thus, the needle holder may be guided along a specific trajectory as defined by the upper ring. This trajectory may include an arc-shaped portion (or a slanted portion) and the means to guide the needle positioning unit along this trajectory may comprise a first arc-shaped guide structure and a second arc-shaped guide structure that is not parallel to the first arc-shaped guide structure and may be, for example, positioned relative to each other at an angle of between 5 degrees and 85 degrees. In some embodiments, the distance between the engagement member and a rotation center of the guiding mechanism is larger than a distance between the through hole and the rotation center of the guiding mechanism.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A positioning apparatus comprising:
   a needle holder having a through hole that is adapted to at least partially surround a needle to guide the needle in a longitudinal direction;
   a needle positioning unit having a base part adapted for mounting on a patient and a moving part having at least two degrees of freedom, which holds the needle holder and moves together with the needle holder so as to position the needle holder, and
   an engagement member that fixes a position of the needle holder with respect to the needle positioning unit,
   wherein the needle holder at least partially detachably attaches to the moving part of the needle positioning unit such that the needle holder is adapted to be removed from the moving part of the needle positioning unit without moving the positioning apparatus and while the insertion state of the needle is maintained.

2. The positioning apparatus according to claim 1, wherein the needle holder is adapted to release a needle after needle insertion.

3. The positioning apparatus according to claim 1, wherein the needle holder at least partially detachably attaches to the engagement member.

4. The positioning apparatus according to claim 1, wherein the needle holder and engagement member together at least partially detachably attaches to the moving part of the needle positioning unit.

5. The positioning apparatus according to claim 4, wherein the engagement member is configured to at least partially detachably attach to the needle positioning unit when on the top of the moving part of the needle positioning unit at an angle relative to the top surface of the needle positioning unit.

6. The positioning apparatus according to claim 1, wherein the through hole is configured to provide for release of the needle after being inserted into an object by being guided along the through hole.

7. The positioning apparatus according to claim 1, wherein the portion of the needle holder surrounding the through hole has a C-shape, a U-shape or a semicircle shape.

8. The positioning apparatus according to claim 1, wherein the needle holder is configured to, or is capable of, being divided or deformed, so that the through hole includes an opening that extends in the longitudinal direction of the needle, and
   wherein a width of the opening in a direction perpendicular to the longitudinal direction is larger than or equal to a width of the needle in the direction perpendicular to the longitudinal direction when the needle holder is divided or deformed.

9. The positioning apparatus according to claim 1, further comprising a fixing member on the needle positioning unit and a fixing member on the engagement member,
   wherein one of the fixing member of the needle positioning unit and the fixing member of the engagement member comprises a protruding portion and the other comprises a recessed portion or hole for engaging the needle holder with the needle positioning unit.

10. The positioning apparatus according to claim 1, further comprising a fixing member on the needle positioning unit that comprises one or more inset portions configured to hold a portion of the engagement member.

11. The positioning apparatus according to claim 1, further comprising a fixing member on the needle positioning unit and a fixing member on the engagement member, wherein one of the fixing member of the needle holder and the fixing member of the engagement member comprises a hinging member and the other comprises a hinge receptor for engaging the needle holder with the needle positioning unit.

12. The positioning apparatus according to claim 1, wherein the engagement member comprises a key that is adapted to slideably attach to the needle positioning unit via a keyway located on the needle positioning unit.

13. The positioning apparatus according to claim 1, wherein the needle holder is completely detachable from the needle positioning unit.

14. The positioning apparatus according to claim 1, wherein the needle positioning unit is adapted for use in a non-sterile field while the needle holder is adapted for use in a sterile field.

15. The positioning apparatus according to claim 1, wherein the needle holder comprises an engageable shutter portion that, when engaged, prevents a needle from leaving the through hole.

16. The positioning apparatus according to claim 1, further comprising a plurality of fiducial markers located on the base part of the needle positioning unit.

17. The positioning apparatus according to claim 1, wherein the engagement member comprises a ring portion that detachably attaches to the needle positioning unit, where the outer diameter of the ring portion is larger than an inner diameter of the needle positioning unit.

18. The positioning apparatus according to claim 17, wherein the ring portion of the engagement member has an opening that is at least wide enough for a needle to fit therethrough.

19. The positioning apparatus according to claim 1, wherein the needle holder comprises a needle guidance member which is positioned such that the bottom end of the needle guidance member is within 0 mm to 30 mm of the bottom plane of the positioning apparatus and the top end of the needle guidance member is within 30 mm to 70 mm of the bottom plane of the positioning apparatus.

20. The positioning apparatus according to claim 1, wherein the needle holder comprises a releasing mechanism adapted to release a needle via an energizing mechanism.

21. A multiple needle positioning apparatus comprising:
at least two needle holders, each having a through hole, the through hole adapted to at least partially surround a needle to guide the needles in a longitudinal direction; and
a needle positioning unit including a base part adapted for mounting on a patient and a moving part having at least two degrees of freedom, the moving part holds the at least two needle holders and moves together with the at least two needle holders so as to position the needle holders,
at least two engagement members that fix position of the needle holders with respect to the needle positioning unit, the at least two needle holders being at least partially detachably attached to the moving part of the needle positioning unit,
wherein the apparatus is adapted such that the at least two needle holders can, when sequentially attached to the needle positioning unit, position at least two needles without interfering with each other, and such that each one of the at least two needle holders can be be sequentially removed from the moving part of the needle positioning unit without moving the positioning apparatus and while the insertion state of a sequentially inserted needle is maintained.

\* \* \* \* \*